(12) United States Patent
Ishida et al.

(10) Patent No.: US 11,904,115 B2
(45) Date of Patent: Feb. 20, 2024

(54) CATHETER ASSEMBLY

(71) Applicant: TERUMO KABUSHIKI KAISHA, Tokyo (JP)

(72) Inventors: Masahiro Ishida, Hadano (JP); Shinya Kusunoki, Hakui (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/713,180

(22) Filed: Apr. 4, 2022

(65) Prior Publication Data

US 2022/0226614 A1  Jul. 21, 2022

Related U.S. Application Data

(60) Division of application No. 16/552,066, filed on Aug. 27, 2019, now Pat. No. 11,318,284, which is a
(Continued)

(30) Foreign Application Priority Data

Mar. 16, 2017  (JP) ................. 2017-051420

(51) Int. Cl.
  *A61M 25/06* (2006.01)
  *A61M 25/01* (2006.01)
(52) U.S. Cl.
  CPC .... *A61M 25/0606* (2013.01); *A61M 25/0141* (2013.01); *A61M 25/0693* (2013.01)

(58) Field of Classification Search
  CPC .......... A61M 25/0606; A61M 25/0141; A61M 25/0693; A61M 25/008; A61M 25/0054;
  (Continued)

(56) References Cited

U.S. PATENT DOCUMENTS 3,694,280 A * 9/1972 Hoef ................. A61M 25/0606
  156/84
4,052,989 A  10/1977 Kline
  (Continued)

FOREIGN PATENT DOCUMENTS

EP  0 161 636 A2  11/1985
EP  0 993 839 A1  4/2000
  (Continued)

OTHER PUBLICATIONS

International Searching Authority, "International Search Report," issued in connection with International Patent Application No. PCT/JP2018/010386, dated May 22, 2018.
(Continued)

*Primary Examiner* — James D Ponton
*Assistant Examiner* — Neeraja Gollamudi
(74) *Attorney, Agent, or Firm* — Foley & Lardner LLP

(57) ABSTRACT

A catheter assembly includes: a catheter; and an inner needle inserted through the catheter. The catheter includes: a catheter body; and a flexible portion that is located at a distal portion of the catheter body and forms a most distal portion of the catheter. An elastic modulus of the catheter body is greater than an elastic modulus of the flexible portion. The catheter has a mixed region in which the catheter body and the flexible portion overlap each other in a radial direction.

16 Claims, 19 Drawing Sheets

Related U.S. Application Data continuation of application No. PCT/JP2018/010386, filed on Mar. 16, 2018.

(58) Field of Classification Search
CPC .......... A61M 25/0053; A61M 25/0113; A61M 25/0069; A61M 25/0068; A61M 25/0052; A61M 25/0045; A61M 25/005

See application file for complete search history.

(56) References Cited

U.S. PATENT DOCUMENTS

| | | | | |
|---|---|---|---|---|
| 4,317,445 | A * | 3/1982 | Robinson | A61M 25/0693 D24/112 |
| 4,610,671 | A | 9/1986 | Luther | |
| 4,790,817 | A | 12/1988 | Luther | |
| 5,017,259 | A * | 5/1991 | Kohsai | B29C 57/00 264/248 |
| 5,403,284 | A | 4/1995 | Gross | |
| 5,512,051 | A * | 4/1996 | Wang | A61M 25/104 604/101.02 |
| 5,967,988 | A | 10/1999 | Briscoe et al. | |
| 6,273,876 | B1 * | 8/2001 | Klima | A61M 25/0051 604/264 |
| 7,575,568 | B2 * | 8/2009 | Holman | A61M 25/1034 623/1.11 |
| 8,073,517 | B1 | 12/2011 | Burchman | |
| 2010/0174246 | A1 * | 7/2010 | Bunch | A61M 25/09 604/526 |
| 2011/0160663 | A1 * | 6/2011 | Stout | A61M 25/0693 604/122 |
| 2011/0270229 | A1 * | 11/2011 | Tanaka | A61M 25/0147 604/528 |
| 2013/0184574 | A1 * | 7/2013 | Newhauser, Jr. | A61M 25/0054 600/431 |
| 2015/0231364 | A1 | 8/2015 | Blanchard et al. | |
| 2015/0306347 | A1 | 10/2015 | Yagi | |
| 2016/0175563 | A1 * | 6/2016 | Woehr | A61M 25/0693 604/168.01 |
| 2016/0310704 | A1 | 10/2016 | Ng et al. | |
| 2017/0106099 | A1 * | 4/2017 | Bellinger | C08L 33/02 |

FOREIGN PATENT DOCUMENTS

| | | |
|---|---|---|
| EP | 1 935 447 A1 | 6/2008 |
| GB | 2 416 995 A | 2/2006 |
| JP | H10-179734 A | 7/1998 |
| JP | 2000-005319 A | 1/2000 |
| JP | 2008-043445 A | 2/2008 |
| JP | 2010-011914 A | 1/2010 |
| JP | 2016-214391 A | 12/2016 |
| WO | WO-00/29056 A | 5/2000 |
| WO | WO-2004/030740 A1 | 4/2004 |
| WO | WO-2013/124765 A1 | 8/2013 |
| WO | WO-2015/006383 A2 | 1/2015 |
| WO | WO-2017/017936 A1 | 2/2017 |

OTHER PUBLICATIONS

International Searching Authority, "Written Opinion," issued in connection with International Patent Application No. PCT/JP2018/010386, dated May 22, 2018.

International Searching Report and Written Opinion issued in connection with International Patent Application No. PCT/JP2018/010386, dated May 22, 2018.

Extended European Search Report dated Jan. 28, 2021 in corresponding European Patent Application No. 18766985.8.

European Office Action issued in connection with EP Appl. Ser. No. 18766985.8 dated Aug. 12, 2022.

* cited by examiner

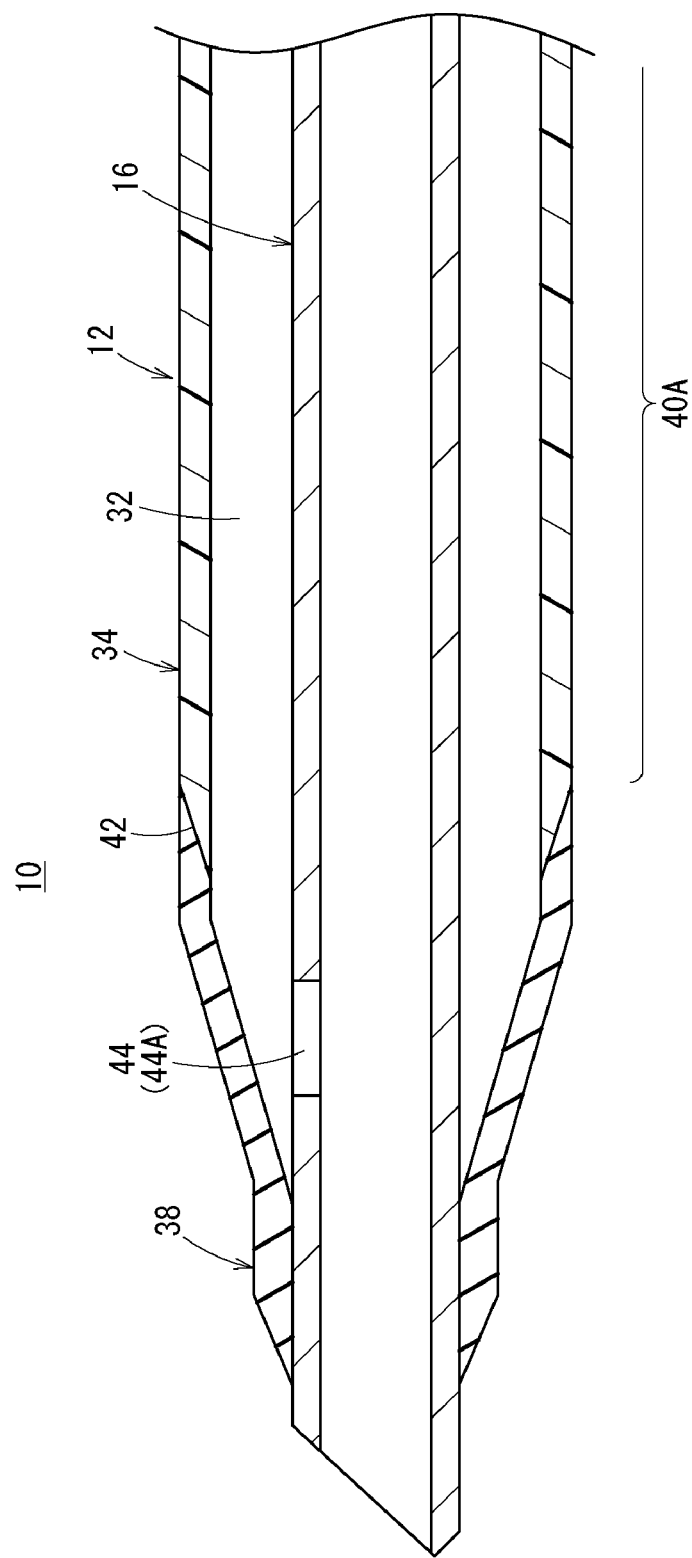

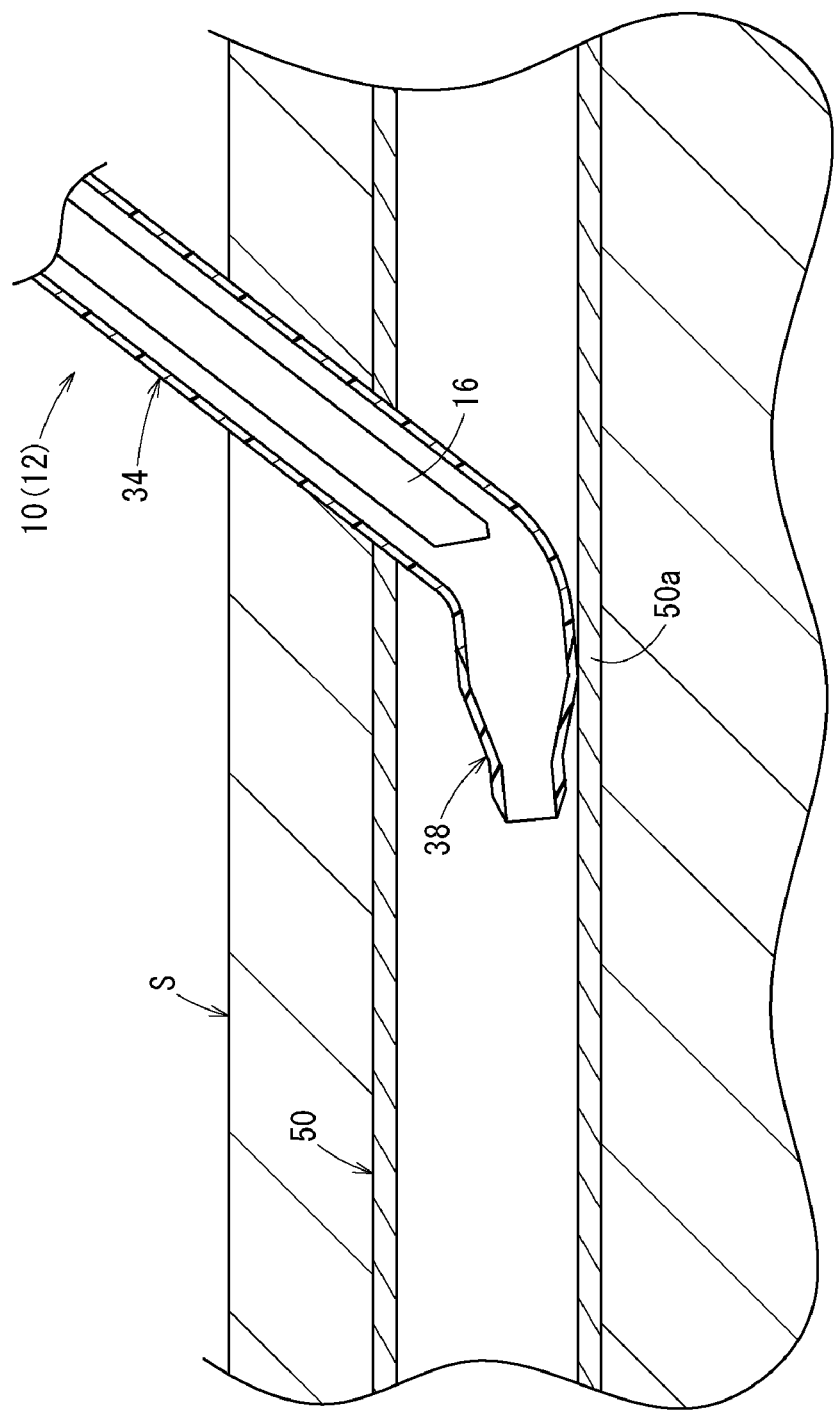

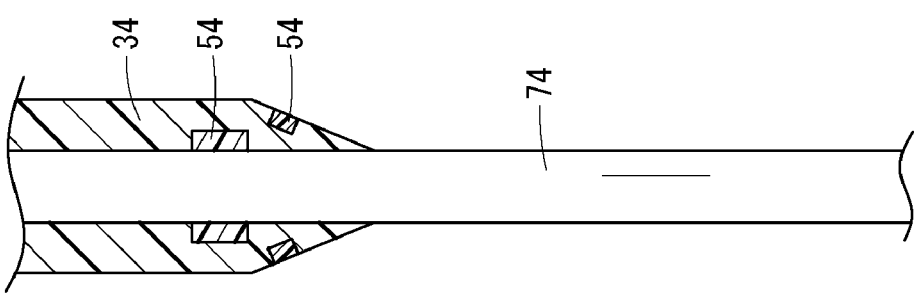
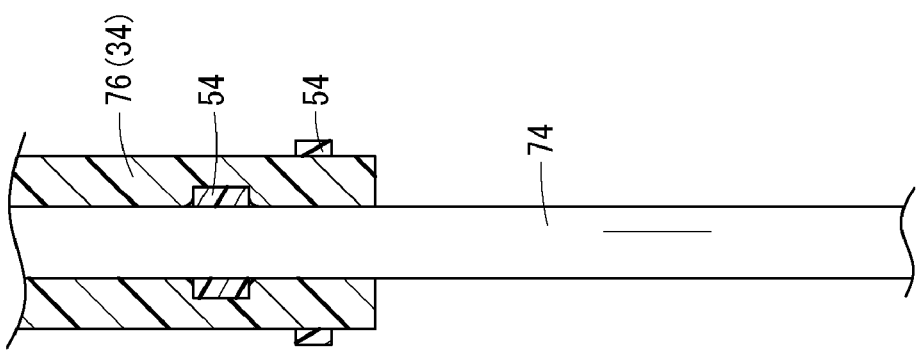
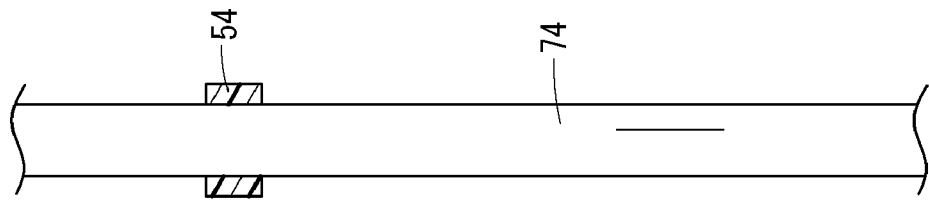

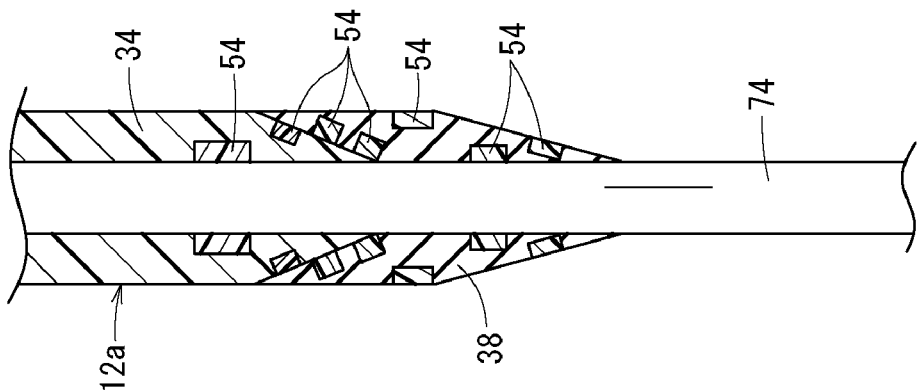
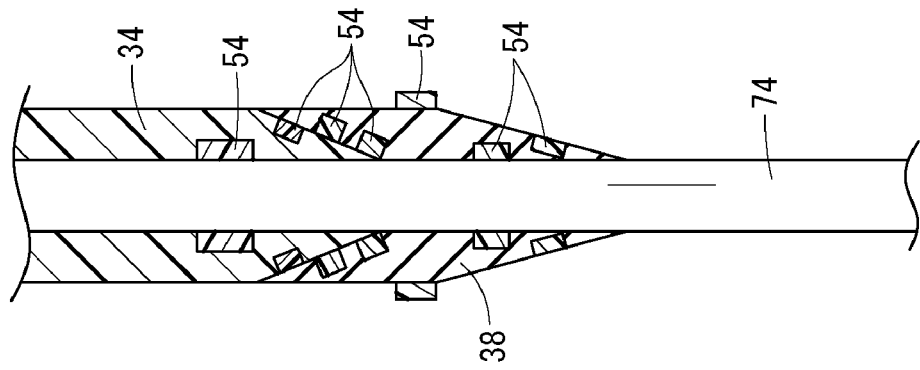

FIG. 18

| | FIRST TAPER ANGLE | SECOND TAPER ANGLE | DISTAL END TIP LENGTH | CURLING | | | SUCTION | PENETRATION RESISTANCE | | STUCK | | |
|---|---|---|---|---|---|---|---|---|---|---|---|---|
| | | | | DETERMINATION | PORK SKIN | COWHIDE | DETERMINATION | DETERMINATION | RESISTANCE VALUE | DETERMINATION | TEST(1) | TEST(2) |
| SAMPLE 1 | 20° | 3° | 0.6mm | OK | OK | OK | OK | OK | 0.2N | NG | 50° | NO DATA |
| SAMPLE 2 | 20° | 3° | 0.7mm | OK | OK | OK | OK | OK | 0.2N | – | 55° | NO DATA |
| SAMPLE 3 | 20° | 3° | 0.8mm | OK | OK | OK | OK | OK | 0.2N | OK | 60° | OK |
| SAMPLE 4 | 20° | 3° | 1.1mm | NG | OK | NG | OK | OK | 0.2N | OK | NO DATA | NO DATA |
| SAMPLE 5 | 20° | 3° | 1.2mm | NG | OK | NG | OK | OK | 0.2N | OK | 65° | NO DATA |
| SAMPLE 6 | 20° | 3° | 1.5mm | NG | NO DATA | NG | OK | OK | 0.2N | OK | NO DATA | NO DATA |
| SAMPLE 7 | 20° | 5° | 0.6mm | OK | OK | OK | OK | OK | 0.2N | NG | 50° | NO DATA |
| SAMPLE 8 | 20° | 5° | 0.7mm | OK | OK | NG | OK | OK | 0.2N | – | 55° | NO DATA |
| SAMPLE 9 | 20° | 5° | 1.1mm | NG | OK | OK | OK | OK | 0.2N | OK | 60° | NO DATA |
| SAMPLE 10 (WITHOUT FLEXIBLE PORTION) | 20° | 4° | | OK | OK | OK | OK | OK | 0.2N | NG | 50° | NG |

CATHETER ASSEMBLY

CROSS-REFERENCE TO RELATED APPLICATIONS

This is a Divisional of U.S. patent application Ser. No. 16/552,066, filed on Aug. 27, 2019, which is a bypass continuation of PCT Application No. PCT/JP2018/010386, filed on Mar. 16, 2018, which claims priority to Japanese Application No. 2017-051420, filed on Mar. 16, 2017. The contents of these applications are hereby incorporated by reference in their entireties.

BACKGROUND

The present disclosure relates to a catheter assembly configured to be punctured and remain indwelled in a blood vessel when performing an infusion or the like to a patient, for example.

Conventionally, a catheter assembly used when performing an infusion or the like to a patient has been known. This kind of catheter assembly includes a hollow catheter, a catheter hub fixed to a proximal end of the catheter, a hollow inner needle that is inserted into the catheter and has a sharp needle tip at a distal end, and a needle hub fixed to a proximal end of the inner needle (for example, see JP 2008-43445 A). When using a catheter assembly, skin and a blood vessel of a living body are punctured with each distal end of the inner needle and the catheter, and then, the catheter is advanced with respect to the inner needle so that the catheter is inserted into the blood vessel by a predetermined length.

SUMMARY

In a conventional catheter assembly having an inner needle and a catheter, a catheter distal end is sometimes caught by a blood vessel back wall (a blood vessel wall opposing a puncture site) when a puncture angle is large. As a result, the catheter may be difficult to insert into a blood vessel, or the blood vessel wall may be damaged by the catheter distal end.

Certain embodiments of the present disclosure have been developed in consideration of such problems, and one object thereof is to provide a catheter assembly capable of deterring a catheter distal end from being caught by a blood vessel back wall at the time of advancing a catheter to a blood vessel even when a puncture angle is large.

According to one embodiment, a catheter assembly includes: a catheter; and an inner needle inserted into the catheter. The catheter includes: a catheter body; and a flexible portion that is provided at a distal portion of the catheter body, includes a most distal portion of the catheter, and is more flexible than the catheter body.

According to the catheter assembly having the above configuration, the flexible portion, which is more flexible than the catheter body, is provided at the distal portion of the catheter body, and thus, it is possible to deter a distal end of the catheter from being caught by a blood vessel back wall even when a puncture angle is large. As a result, it is possible to deter the catheter from being difficult to insert into a blood vessel, or to deter a blood vessel wall from being damaged by the catheter distal end.

A flow path for flashback confirmation may be formed between the catheter and the inner needle, the inner needle may be provided with an introduction path that communicates with the flow path to introduce blood into the flow path, and a proximal end of the introduction path may be provided on a proximal side of an axial center position of a portion of the flexible portion present on a distal side of a most distal portion of the catheter body.

With this configuration, it is possible to deter the catheter from blocking the introduction path at the time of puncture, and thus, it is possible to easily confirm the flashback of blood.

A flow path for flashback confirmation may be formed between the catheter and the inner needle, the inner needle may be provided with an introduction path that communicates with the flow path to introduce blood into the flow path, the catheter may have a close contact portion where at least a part of an inner peripheral surface is in close contact with an outer peripheral surface of the inner needle, and at least a proximal end of the introduction path may be provided on a proximal side of the close contact portion.

With this configuration, it is possible to deter the catheter from blocking the introduction path at the time of puncture, and thus, it is possible to easily confirm the flashback of blood.

The catheter may have a close contact portion where at least a part of an inner peripheral surface is in close contact with an outer peripheral surface of the inner needle, and both the flexible portion and the catheter body may be in close contact with the inner needle at the close contact portion.

With this configuration, an appropriate fitting force between the inner needle and the catheter can be obtained.

The catheter may have a mixed region in which the catheter body and the flexible portion overlap each other in a radial direction.

With this configuration, a change in rigidity from the catheter body to the flexible portion can be made gradual, and thus, it is possible to more favorably deter the catheter distal end from being caught by the blood vessel back wall at the time of inserting the catheter into the blood vessel.

An axial length of the portion of the flexible portion present on the distal side of the most distal portion of the catheter body may be 0.3 to 5.0 mm.

With this configuration, it is possible to suppress curling of the distal end (flexible portion) of the catheter at the time of puncture. In addition, it is possible to more preferably suppress the catching by the blood vessel back wall at the time of inserting the catheter. Further, it is possible to suppress crushing of the catheter distal end at the time of blood suction.

The catheter may have a mixed region in which the catheter body and the flexible portion overlap each other in a radial direction, and an interface between the catheter body and the flexible portion in the mixed region may be formed in a tapered shape inclined with respect to an axis of the catheter.

With this configuration, the change in rigidity from the catheter body to the flexible portion can be made more gradual.

A boundary between the catheter body and the flexible portion or a boundary between a first flexible portion and a second flexible portion may be coated. The whole catheter may be coated seamlessly.

With this configuration, it is possible to eliminate a step between the catheter body and the flexible portion on an inner peripheral surface and an outer peripheral surface of the catheter. Because the step is eliminated, it is possible to deter thrombus and to reduce a penetration resistance at the time of puncture.

A creep strain of the catheter body may be greater than a creep strain of the flexible portion.

With this configuration, the catheter body is easily adapted to a shape of the blood vessel after the catheter is inserted into the blood vessel to remain indwelled. Thus, it is possible to reduce a sense of incompatibility given to the patient during indwelling of the catheter. In addition, crushing of the catheter distal end can be reduced.

The interface between the catheter body and the flexible portion may be provided with a region having a different acoustic impedance from the catheter body and the flexible portion.

With this configuration, the above-described region having the different acoustic impedance functions as an echogenic portion, and thus, it is possible to improve the visibility of the distal portion of the catheter under ultrasound fluoroscopy.

At least the flexible portion between the catheter body and the flexible portion may be provided with a deformation suppressing member that suppresses a radial deformation.

With this configuration, it is possible to suppress curling of the catheter distal end (flexible portion) at the time of puncture, and to suppress crushing of the catheter distal end at the time of blood suction.

The inner needle may be provided with a backcut portion.

A cover may be provided on an outer surface of the flexible portion, and a friction coefficient of a surface of the cover may be set to be smaller than a friction coefficient of a surface of the flexible portion.

A cover may be provided on an outer surface of the flexible portion and an outer surface of the catheter body, a friction coefficient of a surface of the catheter body may be smaller than a friction coefficient of a surface of the flexible portion, and a friction coefficient of a surface of the cover may be smaller than the friction coefficient of the surface of the catheter body.

At least a part of the flexible portion may be in close contact with the inner needle.

According to the catheter assembly of the present invention, it is possible to deter the catheter distal end from being caught by the blood vessel back wall at the time of advancing the catheter to the blood vessel even when the puncture angle is large.

The flexible portion may have a flexible tapered portion that is inclined with respect to the axis of the catheter such that an outer diameter decreases in a distal direction, the flexible tapered portion may have a first flexible tapered portion including the most distal portion and a second flexible tapered portion provided to be adjacent to a proximal side of the first flexible tapered portion, and an inclination angle of an outer peripheral surface of the first flexible tapered portion with respect to the axis may be larger than that of the second flexible tapered portion.

With this configuration, the first flexible tapered portion is relatively thick, and thus, it is possible to suppress the curling of the catheter distal end at the time of puncture. The second flexible tapered portion has the relatively small inclination angle, and thus, the penetration resistance can be reduced.

The catheter body may have a body tapered portion that is inclined with respect to the axis of the catheter such that an outer diameter decreases in the distal direction and is arranged on a radially inner side of the flexible tapered portion, the body tapered portion may have a first body tapered portion and a second body tapered portion provided to be adjacent to a proximal side of the first body tapered portion, and an inclination angle of an outer peripheral surface of the first body tapered portion with respect to the axis may be larger than that of the second body tapered portion.

With this configuration, the inclination angle of the first body tapered portion is relatively large, and thus, it is possible to support the flexible portion from the inner side at the time of blood suction and to suppress a collapse of the flexible portion. Because the inclination angle of the second body tapered portion is relatively small, the gradual transition from a physical property of the flexible portion to a physical property of the catheter body becomes possible, and a kink of the catheter can be suppressed.

The inclination angle of the first body tapered portion may be smaller than the inclination angle of the first flexible tapered portion.

An inner peripheral surface of the flexible tapered portion and an inner peripheral surface of the first body tapered portion may be in close contact with the outer peripheral surface of an inner needle.

With this configuration, an appropriate fitting force between the inner needle and the catheter can be obtained.

A flow path for flashback confirmation may be formed between the catheter and the inner needle, the inner needle may be provided with a side hole that communicates with the flow path and to introduce blood into the flow path, and the side hole may be provided on a proximal side of a most distal portion of the body tapered portion.

With this configuration, the side hole is provided at a position opposing the relatively hard catheter body. Therefore, it is possible to deter the catheter from blocking the side hole at the time of puncture, and thus, it is possible to easily confirm the flashback of blood.

The distal portion of the catheter may have a close contact portion in close contact with an outer peripheral surface of the inner needle, the outer peripheral surface of the inner needle may be provided with an ultrasound reflection promoting portion having an uneven shape, and a distal portion of the ultrasound reflection promoting portion may be provided on a proximal side of a proximal portion of the close contact portion.

With this configuration, the close contact portion and the ultrasound reflection promoting portion do not overlap each other so that the uneven shape of the ultrasound reflection promoting portion does not contribute to a resistance at the time of removing the inner needle, and the removal operation is stabilized.

The flexible portion may have a color that is more easily visible than the catheter body, and the catheter body may have transparency that allows an inside of the catheter body to be visible.

Because the flexible portion is colored to be easily noticeable while securing the flashback visibility by giving the transparency to the catheter body, it is easy to perform puncture with respect to a target blood vessel. In addition, it is easy to understand that the flexible portion is provided at the distal portion of the catheter, and thus, it is possible to appeal to a user that a function of deterring a blood vessel injury is high.

The flexible portion may have a higher X-ray contrast property than the catheter body.

It is possible to enhance the contrast property by X-rays at the time of breaking the catheter while securing the flashback visibility by setting the flexible portion to have the higher X-ray contrast property than the catheter body.

A deflection suppressing mechanism that is capable of supporting the catheter at the time of puncture and suppresses deflections of the inner needle and the catheter may be provided, and the deflection suppressing mechanism may be arranged on a proximal side of the flexible portion in an initial state of the catheter assembly.

With this configuration, it is possible to deter the deflection suppressing mechanism from damaging the flexible portion at the time of advancing the catheter with respect to the inner needle.

BRIEF DESCRIPTION OF DRAWINGS

FIG. 4 is a cross-sectional view of a distal portion in yet another configuration of the catheter assembly;

FIG. 5 is an explanatory view of a function of the catheter assembly;

FIG. 9A is a first explanatory view of a method of manufacturing the catheter, FIG. 9B is a second explanatory view of the method of manufacturing the catheter, and FIG. 9C is a third explanatory view of the method of manufacturing the catheter;

FIG. 11A is a seventh explanatory view of the method of manufacturing the catheter, and FIG. 11B is an eighth explanatory view of the method of manufacturing the catheter;

FIG. 18 is a table illustrating test results associated with the catheter assembly illustrated in FIG. 17.

DETAILED DESCRIPTION

Hereinafter, preferred embodiments of a catheter assembly according to the present invention will be described with reference to the accompanying drawings.

Figure 1:
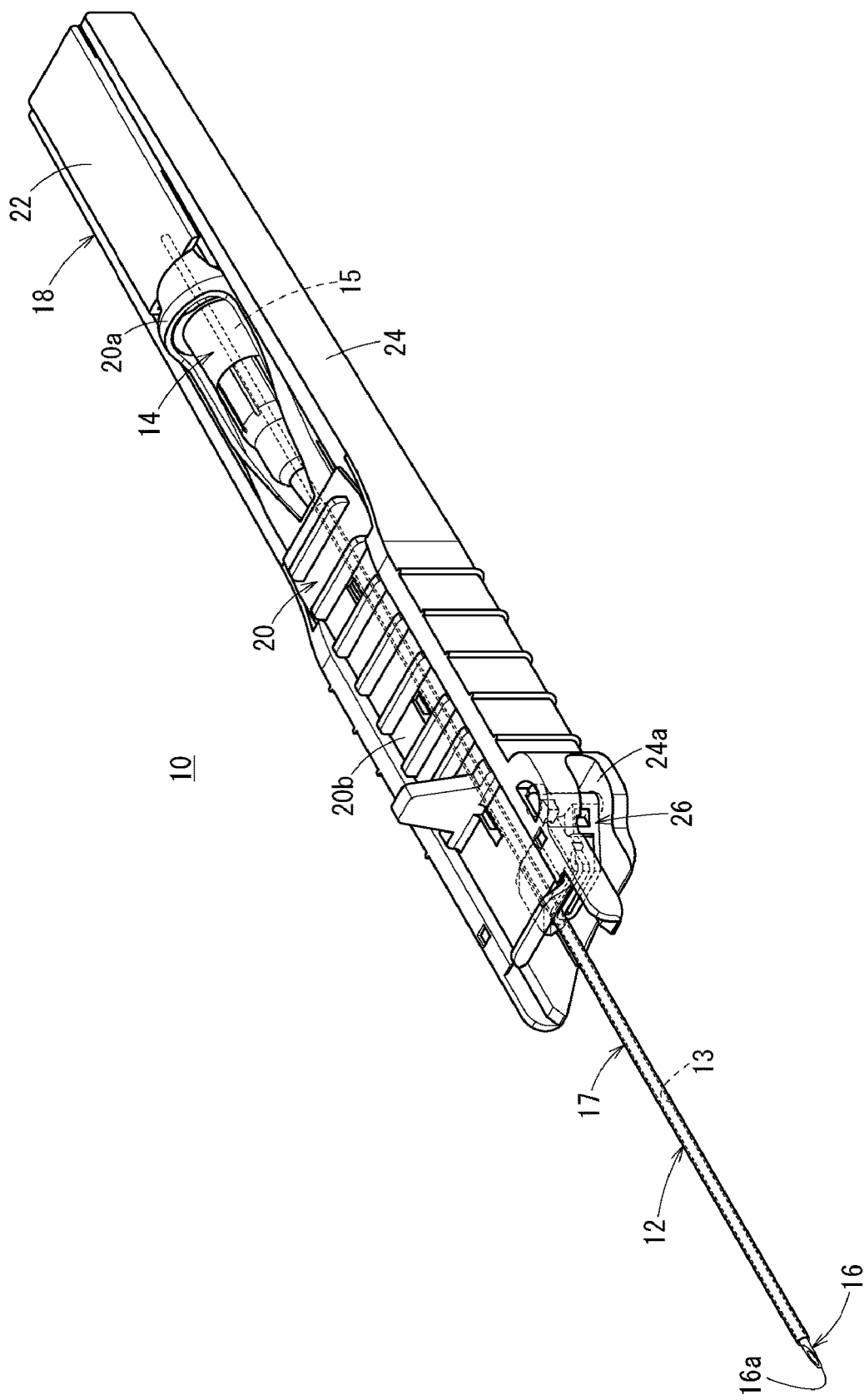
FIG. 1 is a perspective view of a catheter assembly according to an embodiment of the present invention.

The catheter assembly 10 whose initial state is illustrated in FIG. 1 is applied when performing an infusion, a blood transfusion, and the like to a patient (living body), and constructs an introduction portion of a medicinal liquid or the like by being tapped into the patient's body to remain indwelled. The catheter assembly 10 may be configured as a catheter (for example, a central venous catheter, a PICC, a mid-line catheter, and the like) having a longer length than a peripheral venous catheter. Incidentally, the catheter assembly 10 may be configured as the peripheral venous catheter. In addition, the catheter assembly 10 is not limited to the venous catheter, and may be configured as an arterial catheter such as a peripheral arterial catheter.

As illustrated in FIG. 1, the catheter assembly 10 includes a catheter 12, a catheter hub 14 fixedly holding the catheter 12, a hollow inner needle 16 removably inserted into the catheter 12, a needle hub 18 fixedly holding the inner needle 16, and a catheter operation member 20 mounted to the catheter hub 14. The inner needle 16 may be a solid needle.

The catheter assembly 10 forms a multi-tube structure (multi-tube portion) in which the catheter 12 and the inner needle 16 are sequentially stacked in an initial state before use.

The catheter 12 has flexibility and in which a lumen 13 is formed to penetrate therethrough. The lumen 13 is formed to have a diameter capable of housing the inner needle 16 and capable of causing a medicinal liquid, blood, or the like to flow. A distal end of the catheter 12 is reduced in diameter in order to decrease a puncture resistance, and an inner surface of the catheter 12 is in close contact with an outer surface of the inner needle 16 at such a reduced diameter portion in the initial state of the catheter assembly 10. A length of the catheter 12 is not particularly limited but can be appropriately designed according to use and various conditions, and is set to, for example, about 14 to 500 mm, about 30 to 400 mm, or about 76 to 200 mm.

A proximal portion of the catheter 12 is fixed to a distal portion inside the catheter hub 14. The catheter 12 and the catheter hub 14 form a catheter member 17.

The catheter hub 14 is exposed on the patient's skin in a state where the catheter 12 has been inserted into a blood vessel, and indwelled together with the catheter 12 by being pasted with a tape or the like. The catheter hub 14 is formed in a tubular shape tapered in a distal direction.

A constituent material of the catheter hub 14 is not particularly limited, but a thermoplastic resin, such as polypropylene, polycarbonate, polyamide, polysulfone, polyarylate, a methacrylate-butylene-styrene copolymer, and polyurethane may be preferably applied.

A hollow portion 15 that communicates with the lumen 13 of the catheter 12 and through which an infusion solution can flow is provided inside the catheter hub 14. A hemostatic valve, a plug, or the like (not illustrated) may be housed inside the hollow portion 15 in order to deter back-flow of blood at the time of puncture with the inner needle 16 and to allow infusion along with insertion of a connector of an infusion tube.

The inner needle 16 is configured as a hollow tube having rigidity that enables puncture of a skin of a living body, and is arranged to penetrate through the lumen 13 of the catheter 12 and the hollow portion 15 of the catheter hub 14. The inner needle 16 is formed to have a total length longer than that of the catheter 12, and a sharp needle tip 16a is provided at a distal end thereof. A lumen penetrating in an axial direction of the inner needle 16 is provided inside the inner needle 16, and this lumen communicates with a distal opening of the inner needle 16.

Examples of a constituent material of the inner needle 16 include a metal material such as stainless steel, aluminum or an aluminum alloy, and titanium or a titanium alloy, a hard resin, ceramics, and the like.

The needle hub 18 has a needle holding member 22 fixed to a proximal portion of the inner needle 16, and a housing 24 to which the needle holding member 22 is fixed and that extends along the inner needle 16 and the catheter 12. The catheter assembly 10 houses a part of the multi-tube portion, the catheter hub 14, and the catheter operation member 20 in the housing 24 in the initial state. Resin materials forming the needle holding member 22 and the housing 24 are not particularly limited, but, for example, the materials exemplified for the catheter hub 14 can be appropriately selected. Incidentally, the needle holding member 22 and the housing 24 may be integrally formed.

When the needle hub 18 is moved to a proximal direction with respect to the catheter 12, the inner needle 16 is also moved in the proximal direction with respect to the catheter 12 along with the movement of the needle hub 18 because the needle hub 18 holds the inner needle 16 at the needle holding member 22.

The catheter operation member 20 is attached to the catheter hub 14. Thus, when the catheter operation member 20 is advanced relative to the needle hub 18, the catheter member 17 is advanced relative to the inner needle 16. The catheter operation member 20 has a hub mounting portion 20a detachably mounted on the catheter hub 14, and an operation plate portion 20b extending from the hub mounting portion 20a along the catheter 12 in the distal direction. Incidentally, the catheter operation member 20 is not necessarily provided in the catheter assembly 10.

The catheter assembly 10 is provided with a support member 26 on the distal side of the housing 24 in order to support a lower side of the catheter 12 held by the catheter operation member 20. The support member 26 is rotatably attached to an arrangement recess portion 24a provided at a distal portion of the housing 24. A distal portion of the catheter operation member 20 and the support member 26 constitute a deflection suppressing mechanism 27.

When the skin is punctured with the inner needle 16 and the catheter 12, the distal portion of the catheter operation member 20 supports the catheter 12 from above and the support member 26 supports the catheter 12 from below, and thus, deflections of the catheter 12 and the inner needle 16 are suppressed. When the catheter operation member 20 is removed out of the housing 24, the support member 26 is rotated toward an outer side of the housing 24 by being pushed by the hub mounting portion 20a, and thus, the catheter hub 14 can be withdrawn from the housing 24 in the distal direction. Incidentally, the support member 26 is not necessarily provided.

Figure 2A:
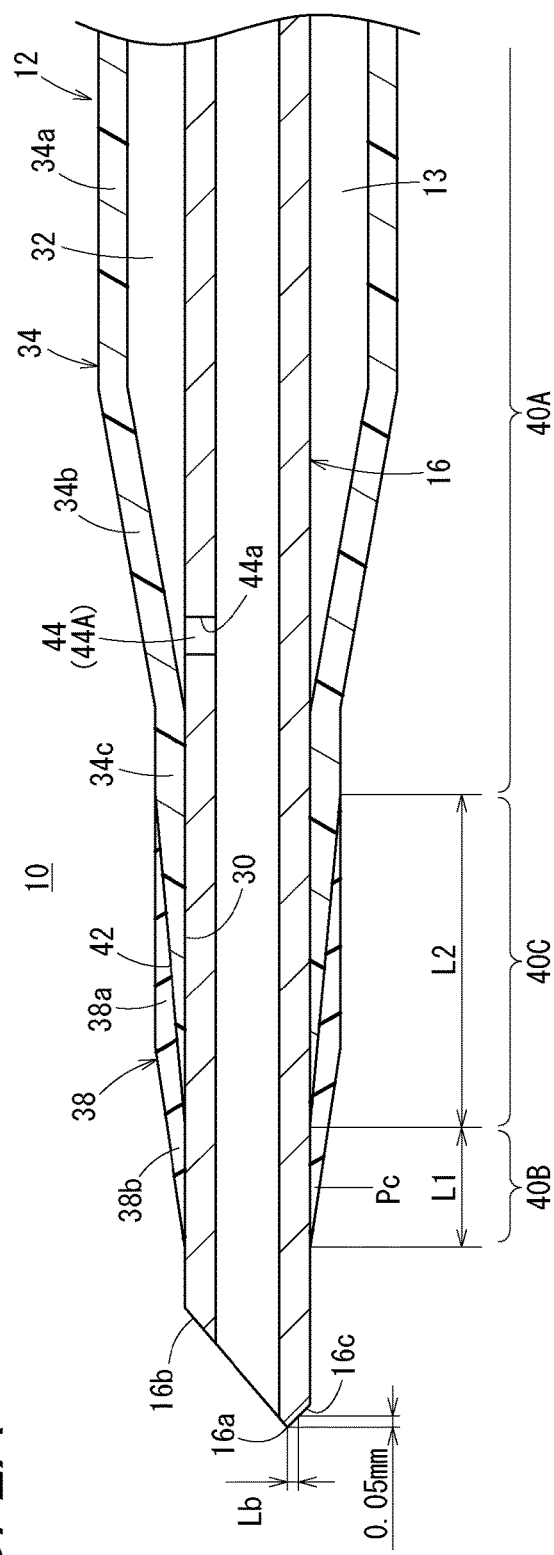
FIG. 2A is a cross-sectional view of a distal portion of the catheter assembly.

As illustrated to FIG. 2A, the catheter 12 has a close contact portion 30, which is in close contact with an outer peripheral surface of the inner needle 16, in at least a part of an inner peripheral surface. The close contact portion 30 is provided on the inner peripheral surface of a distal portion of the catheter 12. A flow path for flashback confirmation (hereinafter, referred to as "flashback flow path 32") is formed between the catheter 12 and the inner needle 16 on the proximal side of the close contact portion 30. The flashback flow path 32 extends up to a proximal opening of the catheter 12.

The catheter 12 has a catheter body 34 that constitutes a main portion of the catheter 12 and a flexible portion 38 provided at a distal portion of the catheter body 34. Thus, the catheter 12 becomes more flexible toward the most distal portion on the distal side. The flexible portion 38 is exposed from the housing 24 (FIG. 1).

The catheter body 34 accounts for most of the whole length of the catheter 12. Thus, the most distal portion of the catheter body 34 is positioned near the most distal end of the catheter 12. The catheter 12 and the flexible portion 38 are made of a resin material having flexibility. A creep strain of the catheter body 34 is greater than a creep strain of the flexible portion 38.

The catheter body 34 has: a straight portion 34a that has a constant outer diameter along the axial direction; a tapered portion 34b that extends from the straight portion 34a in the distal direction and has an outer diameter decreasing in the distal direction; and a distal constituting portion 34c that extends from the tapered portion 34b in the distal direction and constitutes a portion up to the most distal portion of the catheter body 34. An inner peripheral surface of the distal constituting portion 34c and the outer peripheral surface of the inner needle 16 are in close contact with (fitted to) each other in a liquid-tight manner over the entire peripheral.

The flashback flow path 32 is formed between an inner peripheral surface of the catheter body 34 (specifically, the straight portion 34a and the tapered portion 34b) and the outer peripheral surface of the inner needle 16. At least the catheter body 34 between the catheter body 34 and the flexible portion 38 has transparency such that a flashback can be confirmed.

The catheter 12 is supported by the support member 26 (FIG. 1) at a spot of the catheter body 34 (the catheter body 34 is supported by the support member 26). As a result, it is possible to reliably support the catheter 12 and to reduce a sliding resistance at the time of advancing the catheter 12. Moreover, the portion supported by the support member 26 (FIG. 1) is located on the proximal side of an interface 42 between the catheter body 34 and the flexible portion 38, and thus, it is possible to deter peeling of the interface 42 caused by sliding of the catheter 12 with respect to the support member 26.

It is preferably that the catheter body 34 be less likely to swell as compared to the flexible portion 38. As a result, it is possible to set an axial distance between a most distal position of the inner needle 16 and a most distal position of the catheter 12 to a desired size and to reduce a variation for each product during steam sterilization (autoclave sterilization) or ethylene oxide gas sterilization in a process of manufacturing the catheter assembly 10.

Examples of a constituent material of the catheter body 34 include a fluorine-based resin such as polytetrafluoroethylene (PTFE), an ethylene-tetrafluoroethylene copolymer (ETFE), and a perfluoroalkoxy fluorine resin (PFA), an olefin-based resin such as polyethylene and polypropylene or a mixture thereof, polyurethane, polyester, polyamide, a polyether nylon resin, a mixture of the olefin-based resin and an ethylene-vinyl acetate copolymer, and the like. The hardness (Shore A) of the catheter body 34 is, for example, less than 70 D.

The flexible portion 38 forms the most distal portion of the catheter 12. The flexible portion 38 is more flexible than the catheter body 34. That is, an elastic modulus k1 of the catheter body 34 and an elastic modulus k2 of the flexible portion 38 have a relationship of k1>k2.

The flexible portion 38 has: a straight portion 38a that has a constant outer diameter along the axial direction; and a tapered portion 38b that extends from the straight portion 38a in the distal direction and has an outer diameter decreasing in the distal direction. An inner peripheral surface of the flexible portion 38 and the outer peripheral surface of the inner needle 16 are in close contact with (fitted to) each other in a liquid-tight manner over the entire periphery of the inner needle 16.

It is preferable that at least the flexible portion 38 between the catheter body 34 and the flexible portion 38 have an X-ray contrast property. As a result, for example, when the catheter 12 is broken in a blood vessel, it is possible to easily confirm a location of the catheter 12, which has been broken and left in the blood vessel, by X-ray. A contrast layer in the case where the flexible portion 38 has the contrast property may be provided, for example, in any form of a stripe shape, an intermediate layer in the radial direction, or the whole layer.

Examples of a constituent material of the flexible portion 38 include various rubber materials such as natural rubber, butyl rubber, isoprene rubber, butadiene rubber, styrene-butadiene rubber, silicone rubber, various thermoplastic elastomers such as polyurethanes, polyesters, polyamides, olefins, and styrenes or a mixture thereof, and the like.

In the catheter 12, a single catheter body region 40A where only the catheter body 34 between the catheter body 34 and the flexible portion 38 exists, a single flexible portion region 40B where only the flexible portion 38 between the catheter body 34 and the flexible portion 38 exists, and a mixed region 40C where the catheter body 34 and the flexible portion 38 exist are arranged in the axial direction. In the catheter 12 illustrated in FIG. 2A, the interface 42 between the catheter body 34 and the flexible portion 38 is formed in a tapered shape that is inclined at a substantially constant angle with respect to an axis of the catheter 12.

The single catheter body region 40A is a portion of the catheter body 34 present on the proximal side of a most proximal portion of the flexible portion 38.

The single flexible portion region 40B is a portion of the flexible portion 38 present on the distal side of the most distal portion of the catheter body 34. An axial length L1 of the single flexible portion region 40B is set to, for example, 0.3 to 5.0 mm, preferably 0.4 to 2.0 mm, and more preferably 0.5 to 0.9 mm. The hardness of the flexible portion 38 (the single flexible portion region 40B) is, for example, 98 D to 62 D and preferably 46 D to 59 D at 23° C. The flexible portion 38 in the illustrated example is joined to the catheter body 34. Because the axial length and the hardness of the single flexible portion region 40B are set within the above ranges, it is possible to deter the distal end (the flexible portion 38) of the catheter 12 from being curled at the time of puncture. In addition, it is possible to preferably suppress catching by a blood vessel back wall at the time of inserting the catheter 12. Further, it is possible to suppress crushing of the distal end of the catheter 12 at the time of blood suction.

The mixed region 40C is a portion in which the catheter body 34 and the flexible portion 38 are stacked in the radial direction. An axial length L2 of the mixed region 40C is set to, for example, 1 to 5 mm, and preferably 2 to 3 mm.

In the catheter 12 illustrated in FIG. 2A, the interface 42 between the catheter body 34 and the flexible portion 38 is inclined in the distal direction so as to approach the axis (center) of the catheter 12. Thus, the flexible portion 38 is present on the outer side of the catheter body 34 in the mixed region 40C.

The catheter assembly 10 may be provided with a needle protection member that covers the needle tip 16a when the inner needle 16 is removed from the catheter 12. In this case, a protrusion (not illustrated) is provided on the outer peripheral surface of the inner needle 16 to deter the needle protection member from being removed from the inner needle 16 in the distal direction, and the protrusion is preferably provided on the proximal side of the single flexible portion region 40B. As a result, the interface 42 between the catheter body 34 and the flexible portion 38 is not caught by the protrusion at the time of advancing the catheter 12, and it is possible to deter peeling of the interface 42 caused by the protrusion.

The catheter 12 is preferably coated seamlessly with a single coating material on the whole catheter 12 in order to eliminate (or minimize) a step at a boundary between the catheter body 34 and the flexible portion 38 on the inner peripheral surface and an outer peripheral surface of the catheter body 34.

Instead of the above configuration having the interface 42, the catheter 12 may be formed so as to become soft in the distal direction by changing each compounding amount of materials different in hardness in the axial direction. In this case, extrusion molding may be performed while changing each extrusion speed of different materials. Alternatively, a content of a plasticizer at the distal portion of the catheter may be increased. In this case, the plasticizer may be applied to the distal portion of the catheter.

In the inner needle 16, a backcut portion 16c, which is continuous with the needle tip 16a and is inclined in a reverse direction to the blade face 16b with respect to the axis of the inner needle 16, is provided on the opposite side to a blade face 16b. In order to suppress piercing of the inner surface of the catheter 12 by the needle tip 16a when the catheter 12 is retracted after advancing the catheter 12 once with respect to the inner needle 16, a radial length Lb from the needle tip 16a to the backcut portion 16c at a position of 0.05 mm from the needle tip 16a in the proximal direction is set to, for example, 0.01 to 0.05 mm, and more preferably, set to 0.02 to 0.04 mm. It is sufficient if the needle tip 16a is offset to the radially inner side in order to obtain the same effect, and the needle tip 16a may be curved instead of having the backcut portion.

Figure 2B:
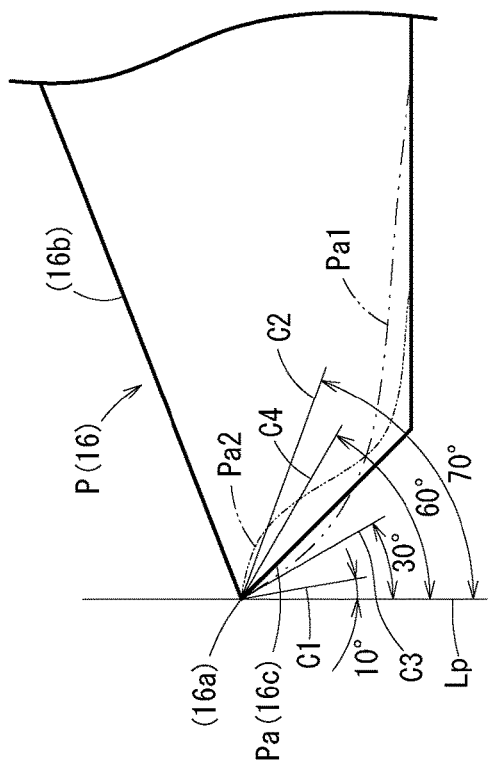
FIG. 2B is an explanatory view of a shape of a distal portion of an inner needle.

As illustrated in FIG. 2B, among projection lines P forming a contour shape of a projection image when the distal portion of the inner needle 16 is projected from just beside, at least a part of a projection line Pa, which corresponds to a portion (the backcut portion 16c in the present embodiment) of the distal portion of the inner needle 16 formed on the opposite side of the blade face 16b and continuous with the needle tip 16a, preferably passes between a straight line C1 at 10° with respect to a straight line Lp, which passes through the needle tip 16a and is perpendicular to a longitudinal direction of the inner needle 16, and a straight line C2 at 70° with respect to the straight line Lp. More preferably, at least a part of the projection line Pa passes between a straight line C3 at 30° with respect to the straight line Lp and a straight line C4 at 60° with respect to the straight line Lp. In FIG. 2B, the projection line Pa is a straight line, the whole projection line Pa passes between the straight line C1 and the straight line C2.

With this configuration, it is possible to achieve both the deterrence of the piercing of the inner surface of the catheter 12 by the needle tip 16a and penetration properties with respect to the skin. When at least a part of the projection line Pa is present in a region closer to the straight line Lp than the straight line C1, the above-described piercing is unlikely to occur, but the penetration resistance becomes large. When at least a part of the projection line Pa is present in a region where an angle with the straight line Lp is larger than an angle with the straight line C4, the penetration resistance is low, but the above-described piercing is likely to occur.

The backcut portion 16c may be formed in a curved shape that bulges toward the straight line Lp like a projection line Pa1. At least a part of the projection line Pa1 preferably passes between the straight line C1 and the straight line C2, and more preferably passes between the straight line C3 and the straight line C4. The backcut portion 16c may be formed in a shape curved in an S shape like a projection line Pa2. At least a part of the projection line Pa2 preferably passes between the straight line C1 and the straight line C2, and more preferably passes between the straight line C3 and the straight line C4.

Figure 3:
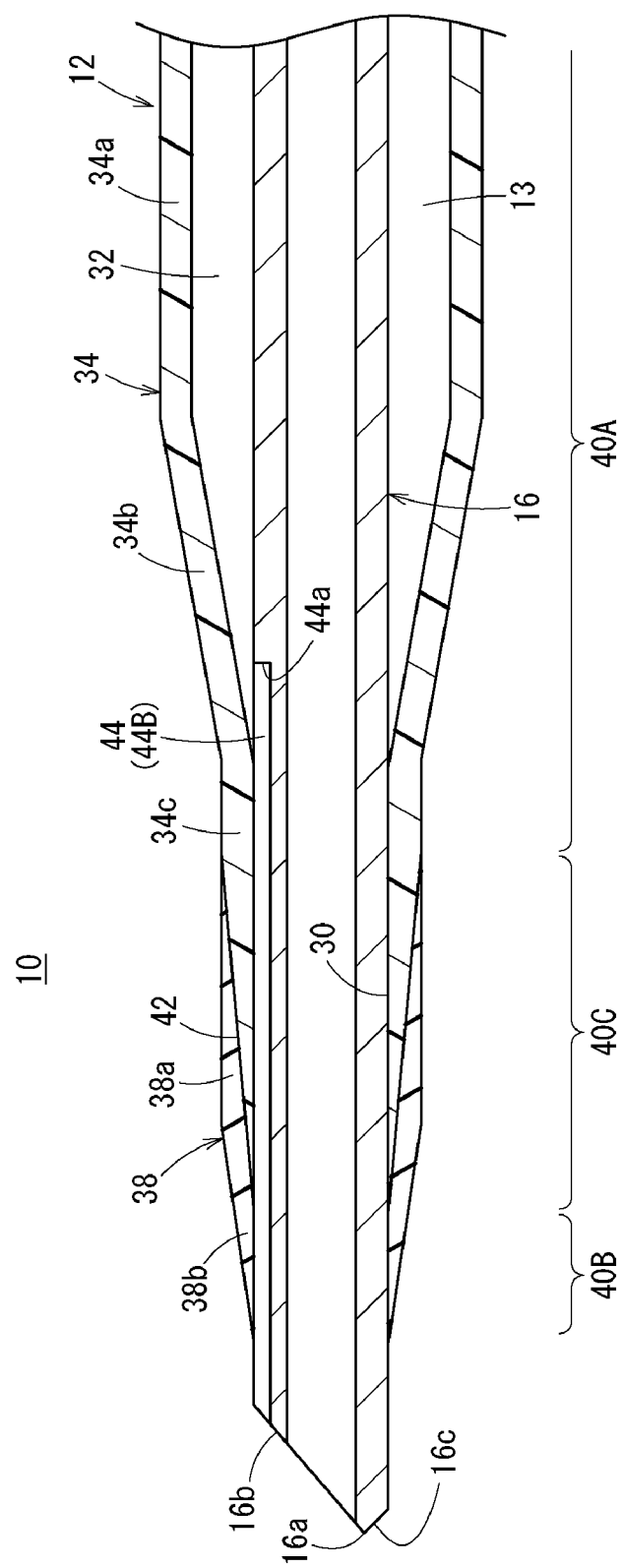
FIG. 3 is a cross-sectional view of a distal portion in another configuration of the catheter assembly.

The inner needle 16 is provided with an introduction path 44 that communicates with the flashback flow path 32 to introduce blood into the flashback flow path 32. The introduction path 44 illustrated in FIG. 2A is a side hole 44A that penetrates through a wall portion of the inner needle 16 in the radial direction. As illustrated in FIG. 3, the introduction path 44 may be a groove portion 44B extending in the axial direction on the outer peripheral surface of the inner needle 16.

In the initial state of the catheter assembly 10 illustrated in FIGS. 2A and 3, a proximal end 44a of the introduction path 44 is provided on the proximal side of an axial center position Pc of the single flexible portion region 40B. More specifically, at least the proximal end 44a of the introduction path 44 is provided on the proximal side of a most distal portion of the single catheter body region 40A. The whole side hole 44A illustrated in FIG. 2A is provided on the proximal side of the most distal portion of the single catheter body region 40A. Incidentally, a part of the side hole 44A may be present on the distal side of the most distal portion of the single catheter body region 40A.

In FIG. 2A, the whole side hole 44A is provided on the proximal side of the mixed region 40C. A part of the side hole 44A may be present on the distal side of a proximal end of the mixed region 40C.

Regarding a position of the introduction path 44 in relation to the close contact portion 30, at least the proximal end 44a of the introduction path 44 (the side hole 44A or the groove portion 44B) is provided on the proximal side of the close contact portion 30 in the initial state of the catheter assembly 10 illustrated in FIGS. 2A and 3. The whole side hole 44A illustrated in FIG. 2A is provided on the proximal side of the close contact portion 30.

As illustrated in FIG. 4, only the inner peripheral surface of the flexible portion 38 between the catheter body 34 and the flexible portion 38 may be in close contact with the outer peripheral surface of the inner needle 16 (the catheter body 34 is not necessarily close contact with the outer peripheral surface of the inner needle 16). In addition, in this case, the whole side hole 44A may be provided on the distal side of the most distal portion (a most distal portion of the interface 42) of the single catheter body region 40A as illustrated in FIG. 4. That is, the side hole 44A may be provided on the inner side of the flexible portion 38. The side hole 44A may have a proximal end positioned on the proximal side of the most distal portion of the single catheter body region 40A and a distal end positioned at the same axial position as the most distal portion or on the distal side of the most distal portion of the single catheter body region 40A.

Next, functions of the catheter assembly 10 configured as described above will be described.

In use of the catheter assembly 10 illustrated in FIG. 1, a puncturing operation to puncture the patient's skin with the catheter assembly 10 is performed. In the puncturing operation, a user (a doctor, a nurse, or the like) presses the distal portion of the catheter assembly 10 against the patient while gripping the housing 24, thereby puncturing the skin toward a puncture target blood vessel. Accordingly, the skin is punctured with the inner needle 16 and each distal portion of the catheter 12.

Next, the user operates the catheter operation member 20 in the distal direction to cause the catheter member 17 (the catheter 12 and the catheter hub 14) to advance while fixing the position of the needle hub 18 (the housing 24). Accordingly, the catheter 12 is inserted to the target position in the blood vessel.

Next, the user pulls the housing 24 in the proximal direction while holding the positions of the catheter operation member 20 and the catheter member 17. Accordingly, the catheter member 17 and the catheter operation member 20 completely come out of the housing 24, and the inner needle 16 is removed from the catheter 12 in the proximal direction.

Next, the catheter operation member 20 is detached from the catheter hub 14. Accordingly, the catheter member 17 is indwelled in the patient. Incidentally, the catheter operation member 20 may be kept attached to the catheter hub 14 depending on a preference of the user.

Next, the connector of the infusion tube (not illustrated) is connected to the proximal side (the proximal portion of the catheter hub 14) of the catheter member 17 from which the inner needle 16 has been removed, and the infusion solution (medicinal liquid) is administered from the infusion tube to the patient.

In this case, the catheter assembly 10 according to the present embodiment has the following effects.

According to the catheter assembly 10, the flexible portion 38, which is more flexible than the catheter body 34, is provided at the distal portion of the catheter body 34 as illustrated in FIG. 2A. Thus, it is possible to deter the distal end of the catheter 12 from being caught by a blood vessel back wall 50a, which is a blood vessel wall of a blood vessel 50 on the opposite side of a puncture spot at the time of advancing the catheter 12 to insert the catheter 12 into the blood vessel 50 after puncturing a skin S with the distal portion of the catheter assembly 10 even when a puncture angle is large as illustrated in FIG. 5.

That is, the flexible portion 38 is brought into contact with the blood vessel back wall 50a and is pressed by the blood vessel back wall 50a to be easily deformed at the time of advancing the catheter 12 as illustrated in FIG. 5, and thus, it is possible to deter the distal end of catheter 12 from being caught by the blood vessel back wall 50a. As a result, it is possible to deter the catheter 12 from being difficult to insert into the blood vessel 50 or to deter the blood vessel back wall 50a from being damaged by the distal end of the catheter 12.

As illustrated in FIG. 2A, the flashback flow path 32 is formed between the catheter 12 and the inner needle 16, and the inner needle 16 is provided with the introduction path 44 that communicates with the flashback flow path 32 to introduce blood into the flashback flow path 32. The proximal end 44a of the introduction path 44 is provided on the proximal side of the axial center position Pc of the portion of the flexible portion 38 present on the distal side of the most distal portion of the catheter body 34. In addition, the catheter 12 has the close contact portion 30 in which at least a part of the inner peripheral surface is in close contact with the outer peripheral surface of the inner needle 16, and at least the proximal end of the introduction path 44 is provided on the proximal side of the close contact portion 30.

With the above configuration, it is possible to deter the flexible portion 38 from being deformed to block the introduction path 44 at the time of puncture, and thus, it is possible to easily confirm the flashback of blood.

In the close contact portion 30, both the flexible portion 38 and the catheter body 34 are in close contact with the inner needle 16. With this configuration, an appropriate fitting force between the inner needle 16 and the catheter 12 can be obtained. With the appropriate fitting force, the flexible portion 38 is deterred from being curled, and the inner needle 16 can be easily removed from the catheter 12 at the time of puncturing the skin.

The catheter 12 has the mixed region 40C in which the catheter body 34 and the flexible portion 38 overlap each other in the radial direction. With this configuration, a change in rigidity from the catheter body 34 to the flexible portion 38 can be made gradual, and thus, it is possible to more favorably deter the distal end of the catheter 12 from being caught by the blood vessel back wall 50a at the time of inserting the catheter 12 into the blood vessel 50.

The axial length of the single flexible portion region 40B (the portion of the flexible portion 38 present on the distal side of the most distal portion of the catheter body 34) is 0.3 to 5.0 mm. With this configuration, it is possible to suppress the curling of the distal end (the flexible portion 38) of the catheter 12 at the time of puncture. In addition, it is possible to more preferably suppress the catching by the blood vessel back wall 50a at the time of inserting the catheter 12. Further, it is possible to suppress crushing of the distal end of the catheter 12 at the time of blood suction.

The interface 42 between the catheter body 34 and the flexible portion 38 in the mixed region 40C is formed in the tapered shape that is inclined with respect to the axis of the catheter 12. With this configuration, the change in rigidity from the catheter body 34 to the flexible portion 38 can be made more gradual.

The whole catheter 12 is coated seamlessly. With this configuration, it is possible to eliminate the step between the catheter body 34 and the flexible portion 38 on the inner peripheral surface and the outer peripheral surface of the catheter 12. Because the step is eliminated, it is possible to deter thrombus and to reduce a penetration resistance at the time of puncture.

A creep strain of the catheter body 34 is greater than a creep strain of the flexible portion 38. With this configuration, the catheter body 34 is easily adopted to a shape of the blood vessel after the catheter 12 is inserted into the blood vessel 50 to remain indwelled. Thus, it is possible to reduce a sense of incompatibility given to the patient during indwelling of the catheter 12. In addition, the flexible portion 38 has the smaller creep strain than the catheter body 34, and thus, can easily return to the original shape even if being deformed. Thus, it is possible to reduce the crushing of the distal end of the catheter 12 caused by the blood suction.

Figure 6A:
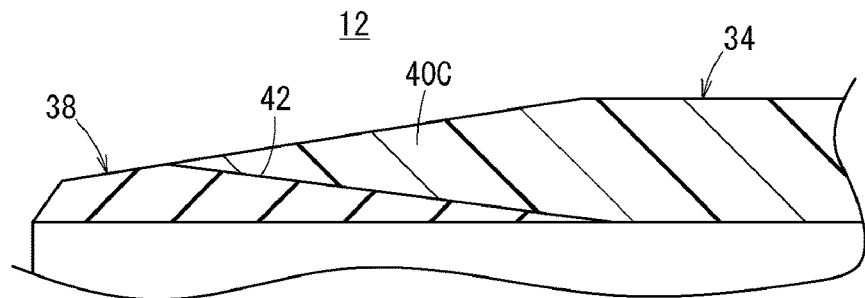
FIG. 6A is a cross-sectional view of a catheter having another interface shape.

As illustrated in FIG. 6A, the interface 42 between the catheter body 34 and the flexible portion 38 may be inclined at a substantially constant angle so as to be separated farther from the axis of the catheter 12 in the distal direction. Even with this configuration, the change in rigidity from the catheter body 34 to the flexible portion 38 can be made gradual similarly to the case in which the interface 42 is inclined at the substantially constant angle so as to approach the axis of the catheter 12 in the distal direction (FIG. 2A).

Figure 6B:
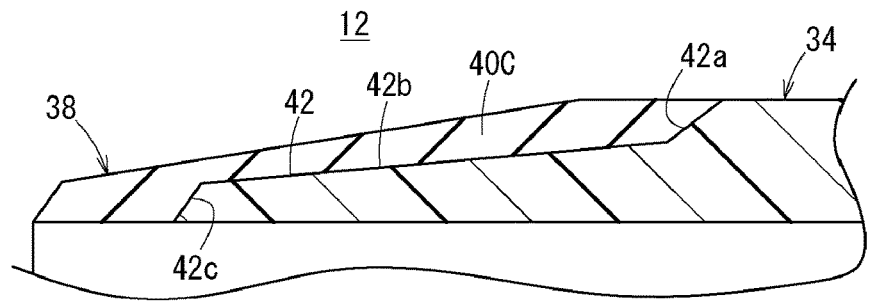
FIG. 6B is a cross-sectional view of a catheter having still another interface shape.

As illustrated in FIG. 6B, the interface 42 may have a plurality of regions aligned in the axial direction, and regions adjacent to each other among the plurality of regions may have different angles with respect to the axis of the catheter 12. With this configuration, it becomes easy to adjust the rigidity in the mixed region 40C in which the catheter body 34 and the flexible portion 38 overlap each other in the radial direction, and thus, the change in rigidity from the catheter body 34 to the flexible portion 38 can be easily adjusted.

In FIG. 6B, the interface 42 is inclined so as to approach the axis of the catheter 12 in the distal direction. Specifically, the interface 42 has: a first region 42a; a second region 42b that is adjacent to the distal side of the first region 42a and is inclined with respect to the first region 42a; and a third region 42c that is adjacent to the distal side of the second region 42b and is inclined with respect to the second region 42b. An angle of the second region 42b with respect to the axis of the catheter 12 is smaller than angles of the first region 42a and the third region 42c with respect to the axis of the catheter 12. The angles of the first region 42a and the third region 42c with respect to the axis of the catheter 12 may be the same or different from each other.

Figure 6C:
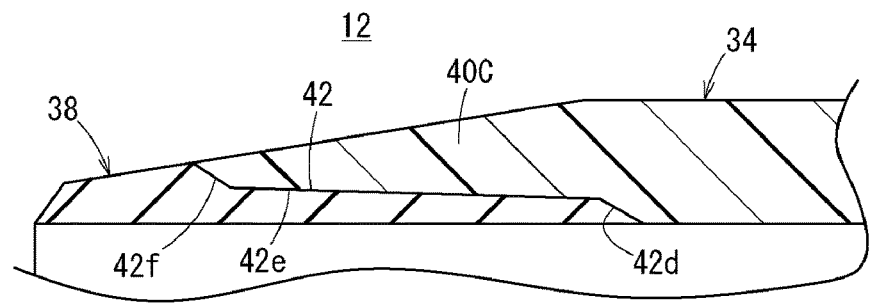
FIG. 6C is a cross-sectional view of a catheter having yet still another interface shape.

As illustrated in FIG. 6C, the interface 42 may be inclined so as to be separated farther from the axis of the catheter 12 in the distal direction and may have a plurality of regions aligned in the axial direction. Even with this configuration, it becomes easy to adjust the rigidity in the mixed region 40C in which the catheter body 34 and the flexible portion 38 overlap each other in the radial direction similarly to the configuration of FIG. 6B, and thus, the change in rigidity from the catheter body 34 to the flexible portion 38 can be easily adjusted.

In FIG. 6C, the interface 42 has: a first region 42d; a second region 42e that is adjacent to the distal side of the first region 42d and is inclined with respect to the first region 42d; and a third region 42f that is adjacent to the distal side of the second region 42e and is inclined with respect to the second region 42e. An angle of the second region 42e with respect to the axis of the catheter 12 is smaller than angles of the first region 42d and the third region 42f with respect to the axis of the catheter 12. The angles of the first region 42d and the third region 42f with respect to the axis of the catheter 12 may be the same as or different from each other.

Figure 6D:
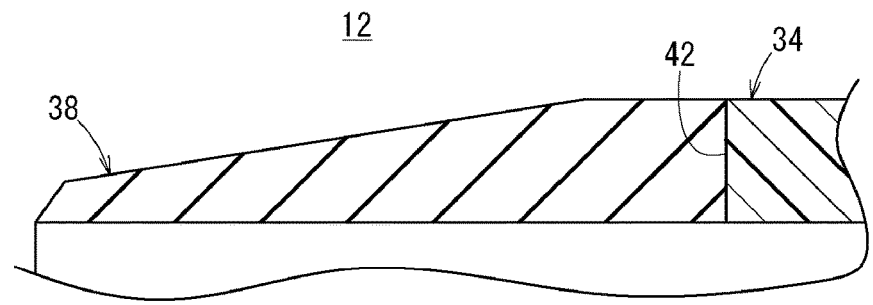
FIG. 6D is a cross-sectional view of a catheter having even yet still another interface shape.

As in FIG. 6D, the interface 42 between the catheter body 34 and the flexible portion 38 may be perpendicular to the axis of the catheter 12.

Figure 7A:
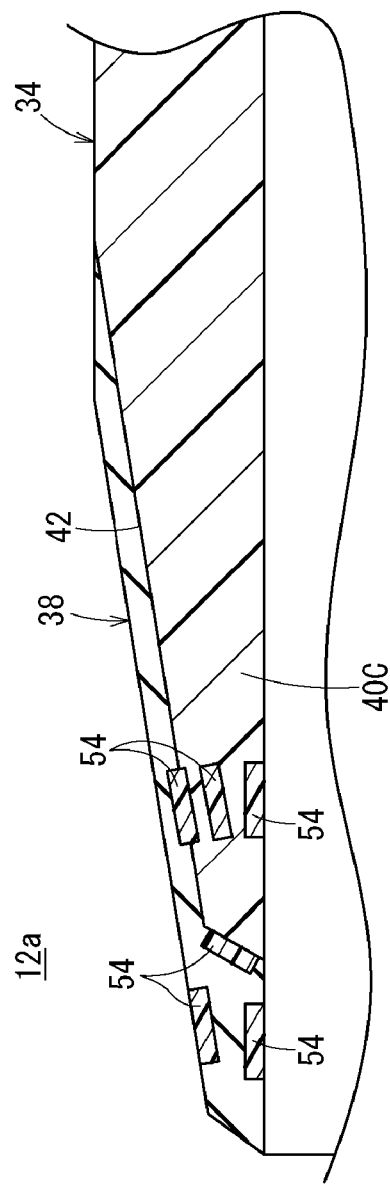
FIG. 7A is a cross-sectional view of a catheter having a deformation suppressing member.
Figure 7B:
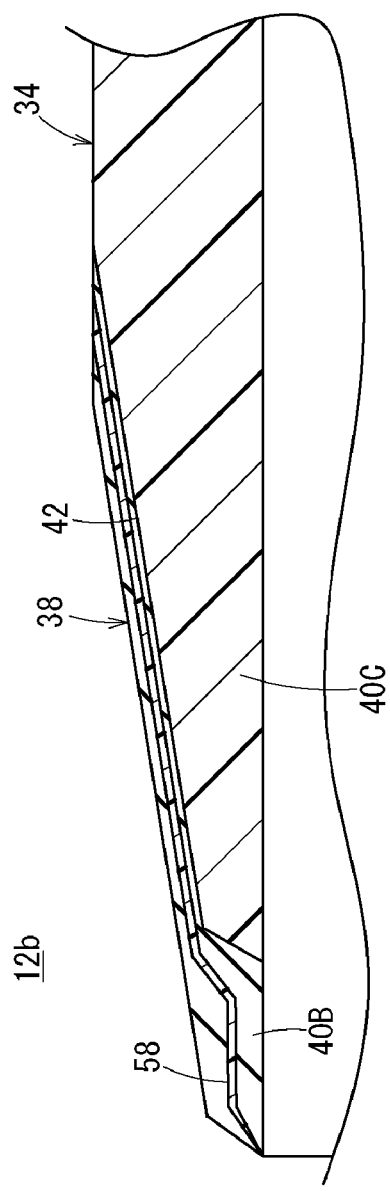
FIG. 7B is a cross-sectional view of a catheter having another deformation suppressing member.

The catheter assembly 10 may employ a catheter 12a illustrated in FIG. 7A or a catheter 12b illustrated in FIG. 7B. In the catheters 12a and 12b illustrated in FIGS. 7A and 7B, deformation suppressing members 54 and 58, respectively, suppressing a radial deformation are provided in at least the flexible portion 38 between the catheter body 34 and the flexible portion 38. With this configuration, it is possible to suppress curling of the distal end (the flexible portion 38) of the catheter 12a or 12b at the time of puncture, and to suppress crushing of the distal end of the catheter 12a or 12b at the time of blood suction. The deformation suppressing member 54 or 58 has a shape that makes at least one turn in a circumferential direction. With this configuration, the radial deformation can be more effectively suppressed.

The catheter 12a illustrated in FIG. 7A is provided with a plurality of the deformation suppressing members 54. Specifically, the deformation suppressing members 54 are provided on the inner peripheral surface, the outer peripheral surface, the inside, and the distal end of the catheter body 34 in the mixed region 40C, and on the inner peripheral surface and the outer peripheral surface of the flexible portion 38, but may be provided at any one spot or a plurality of spots among these sites. The deformation suppressing member 54 provided in the flexible portion 38 is preferably a member harder than the catheter body 34 (a member having a higher elastic modulus). Incidentally, the deformation suppressing member 54 provided in the flexible portion 38 may be a member that has the same hardness as the catheter body 34 or is softer than the catheter body 34.

The deformation suppressing member 54 provided in the flexible portion 38 is preferably a member having a smaller creep strain than the catheter body 34. Incidentally, the deformation suppressing member 54 provided in the flexible portion 38 is preferably a member having a smaller creep strain than the flexible portion 38. When the deformation suppressing member 54 having the small creep strain is provided, the distal end of the catheter 12a is easily restored to the original shape at the time of stopping suction even if blood is suctioned at an excessive speed so that the distal end of the catheter 12a is crushed.

In the catheter 12b illustrated in FIG. 7B, the deformation suppressing member 58 continuously extending from the single flexible portion region 40B over the mixed region 40C is provided concentrically with the catheter 12b. Specifically, the deformation suppressing member 58 is provided inside the flexible portion 38. The deformation suppressing member 58 may be provided on the outer peripheral surface of the flexible portion 38. The deformation suppressing member 58 is preferably a member harder than the catheter body 34 (a member having a higher elastic modulus). Incidentally, the deformation suppressing member 58 may be a member that has the same hardness as the catheter body 34 or is softer than the catheter body 34.

Figure 8:
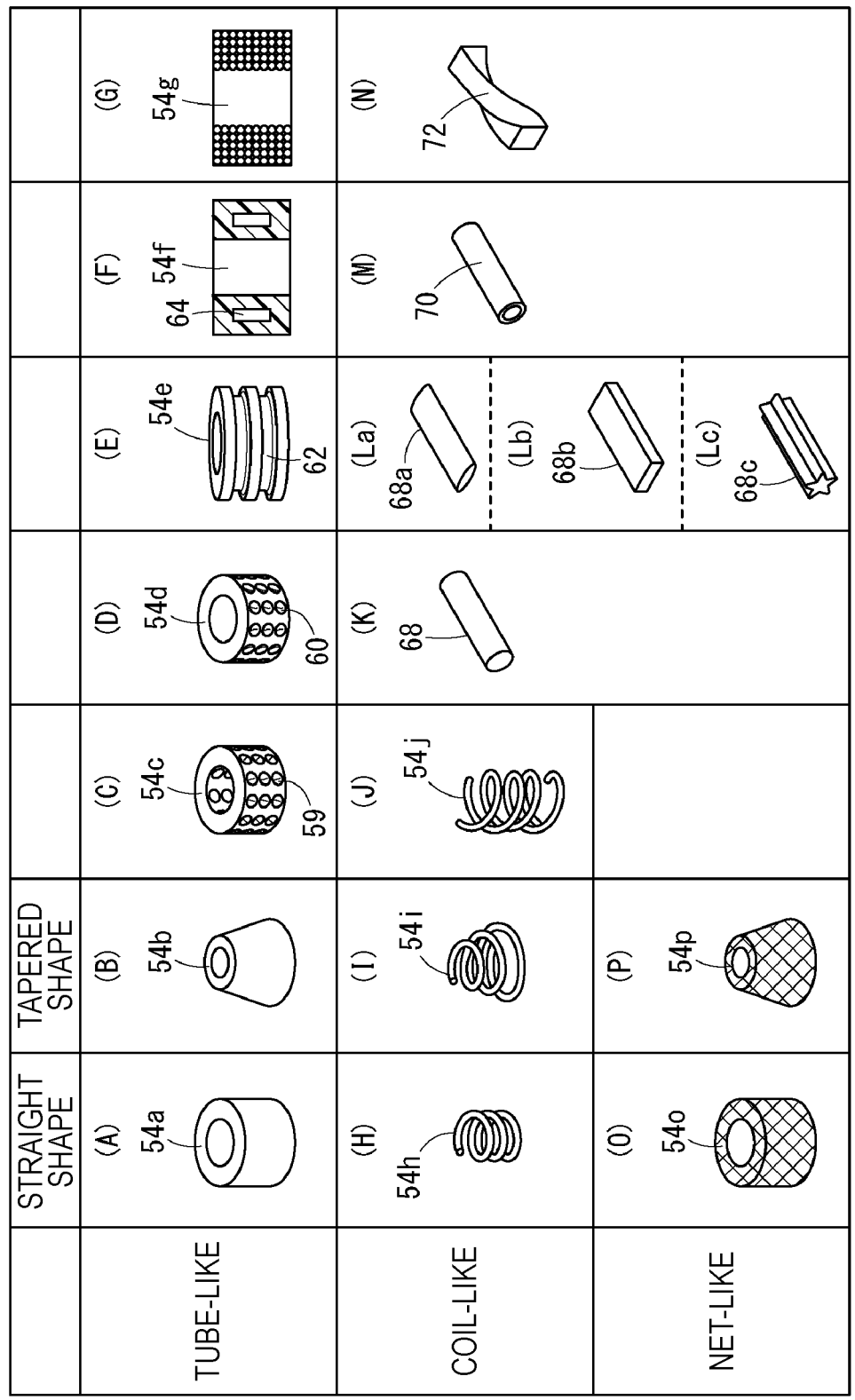
FIG. 8 is an explanatory view of a form variation of the deformation suppressing member.

The deformation suppressing member 54 (or the deformation suppressing member 58) can adopt various forms as illustrated in FIG. 8. Deformation suppressing members 54a to 54g in cells A to G have tube-like (ring-like) forms. Specifically, the deformation suppressing member 54a in the cell A has a straight shape with a constant outer diameter in the axial direction. The deformation suppressing member 54b in the cell B has a tapered shape with an outer diameter changing in the axial direction. The deformation suppressing member 54c in the cell C has a straight shape with a constant outer diameter in the axial direction, and has a large number of through-holes 59 penetrating in the radial direction.

The deformation suppressing member 54d in the cell D has a large number of recess portions 60 on an outer peripheral surface (or an inner peripheral surface). The deformation suppressing member 54e in the cell E has a ring-shaped groove 62 on an outer peripheral surface (or an inner peripheral surface). The deformation suppressing member 54f in the cell F has a cavity 64 inside a circumferential wall. The deformation suppressing member 54g in the cell G is configured using a porous body (for example, a sintered body).

Deformation suppressing members 54h to 54j in cells H to J have coil-like forms. Specifically, the deformation suppressing member 54h in the cell H has a straight shape with a constant outer diameter in the axial direction. The deformation suppressing member 54i in the cell I has a tapered shape with an outer diameter changing in the axial direction. The deformation suppressing member 54j in the cell J is configured in multiple spirals.

Deformation suppressing members 54o and 54p in a cell O and a cell P have tubular net-like forms. Specifically, the deformation suppressing member 54o in the cell O has a straight shape with a constant outer diameter in the axial direction. The deformation suppressing member 54p in the cell P has a tapered shape with an outer diameter changing in the axial direction.

As wires constituting the deformation suppressing members 54h to 54j, 54o, and 54p in the cell H to the cell J, the cell O, and the cell P, a wire 68 having a circular cross section as in the cell K may be used, wires 68a to 68c having non-circular cross sections as in cells La to Lc (an elliptical shape in a cell La, a rectangular shape in a cell Lb, and a star shape in a cell Lc) may be used, a hollow wire 70 as in a cell M may be used, or a twisted wire 72 as in a cell N may be used.

Next, an example of a method of manufacturing the catheter 12 provided with the deformation suppressing member 54 will be described. As illustrated in FIG. 9A, the deformation suppressing member 54 is fitted (mounted) to a core member 74. Next, a first tube member 76, which is a material of the catheter body 34, is mounted to the core member 74, and the other deformation suppressing member 54 is fitted to an outer peripheral surface of a distal portion of the first tube member 76 as illustrated in FIG. 9B. Next, an object is molded by pressing and heating the first tube member 76 and the deformation suppressing members 54 with a mold (not illustrated). As a result, the catheter body 34 formed in a tapered shape with a tapered distal portion as illustrated in FIG. 9C is obtained.

Figure 10A:
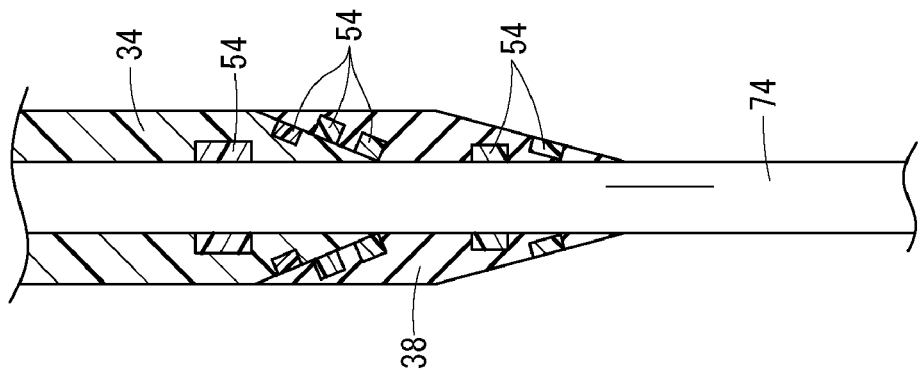
FIG. 10A is a fourth explanatory view of the method of manufacturing the catheter.
Figure 10B:
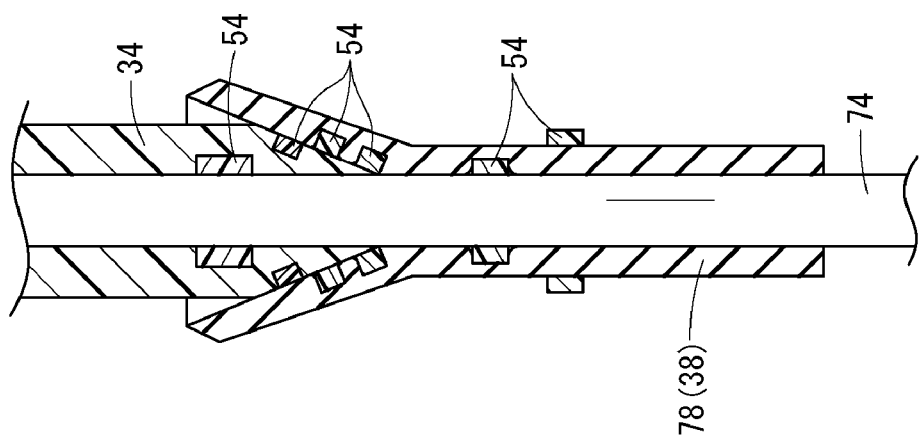
FIG. 10B is a fifth explanatory view of the method of manufacturing the catheter.
Figure 10C:
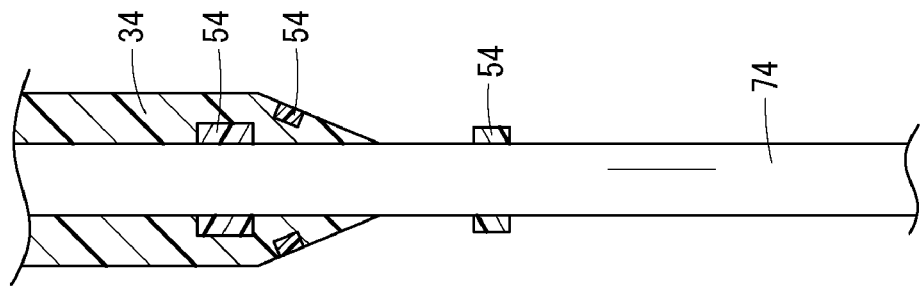
FIG. 10C is a sixth explanatory view of the method of manufacturing the catheter.

Next, the deformation suppressing member 54 is fitted to the core member 74 on the distal side of the catheter body 34 as in FIG. 10A. Next, a second tube member 78, which is a material of the flexible portion 38 and has the other deformation suppressing members 54 mounted on an inner peripheral surface and an outer peripheral surface thereof, is mounted to the core member 74 and the distal portion of the catheter body 34 as illustrated in FIG. 10B. Then, the second tube member 78 and the deformation suppressing member 54 are pressed and heated using a mold (not illustrated) (which may be the same as the mold used at the time of molding the distal portion of the first tube member 76). As a result, the flexible portion 38 formed in a tapered shape with a tapered distal portion as illustrated in FIG. 10C is obtained.

Next, the deformation suppressing member 54 is fitted on the outer peripheral surface of the flexible portion 38 as illustrated in FIG. 11A. Then, the deformation suppressing member 54 is pressed and heated using a mold (not illustrated) (which may be the same as the mold used at the time of molding the distal portion of the first tube member 76 or the second tube member 78) so that the deformation suppressing member 54 is embedded in the outer peripheral surface of the flexible portion 38 as illustrated in FIG. 11B. As a result, the catheter 12a provided with the deformation suppressing members 54 is obtained.

Incidentally, installation spots and the number of the deformation suppressing members 54 can be changed as appropriate in the above method of manufacturing the catheter 12.

As illustrated in FIGS. 12A to 12D, it is also possible to manufacture the second tube member 78 provided with the deformation suppressing member 54 (or the deformation suppressing member 58) by performing blade processing or multi-layer molding at the time of manufacturing the second tube member 78, which is the material of the flexible portion 38.

Figure 12A:
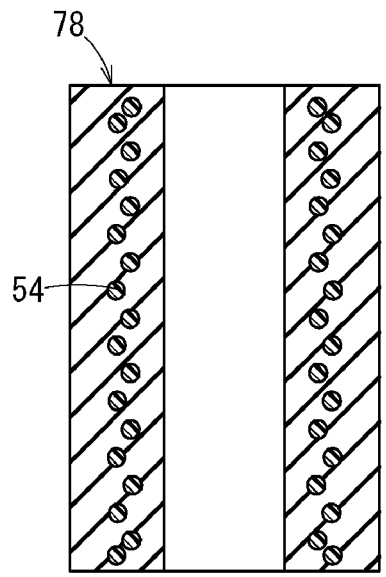
FIG. 12A is an explanatory view of a method of manufacturing a second tube member having a deformation suppressing member.
Figure 12B:
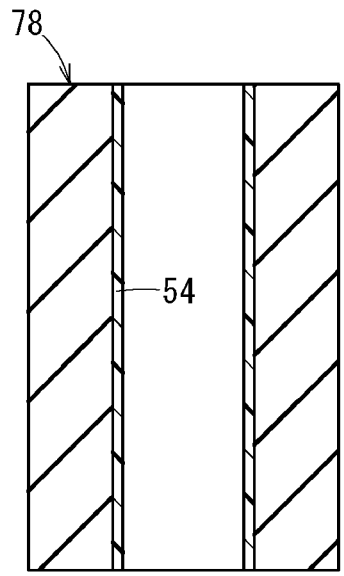
FIG. 12B is an explanatory view of a method of manufacturing another second tube member having a deformation suppressing member.
Figure 12C:
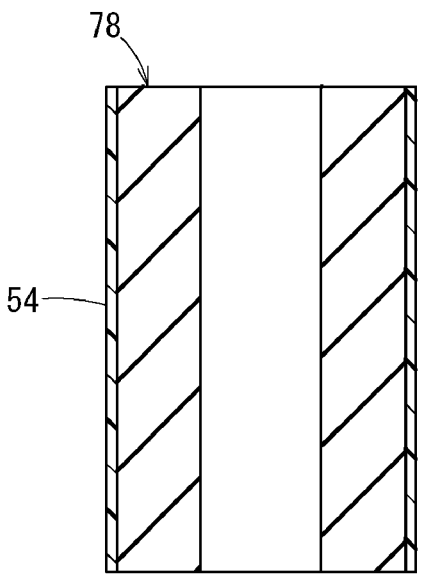
FIG. 12C is an explanatory view of a method of manufacturing still another second tube member having a deformation suppressing member.
Figure 12D:
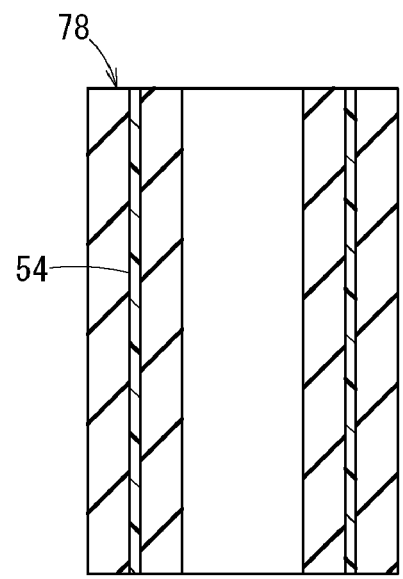
FIG. 12D is an explanatory view of a method of manufacturing yet still another second tube member having a deformation suppressing member.

The second tube member 78 illustrated in FIG. 12A is obtained by forming the deformation suppressing member 54 (see deformation suppressing members 54o and 54p in FIG. 8) having a form of a blade (a tubular net-like member) as an intermediate layer. The second tube member 78 illustrated to FIG. 12B is obtained by forming the deformation suppressing member 54 as an inner layer by multi-layer molding. The second tube member 78 illustrated to FIG. 12C is obtained by forming the deformation suppressing member 54 as an outer layer by multi-layer molding. The second tube member 78 illustrated to FIG. 12D is obtained by forming the deformation suppressing member 54 as an intermediate layer by multi-layer molding.

Figure 13:
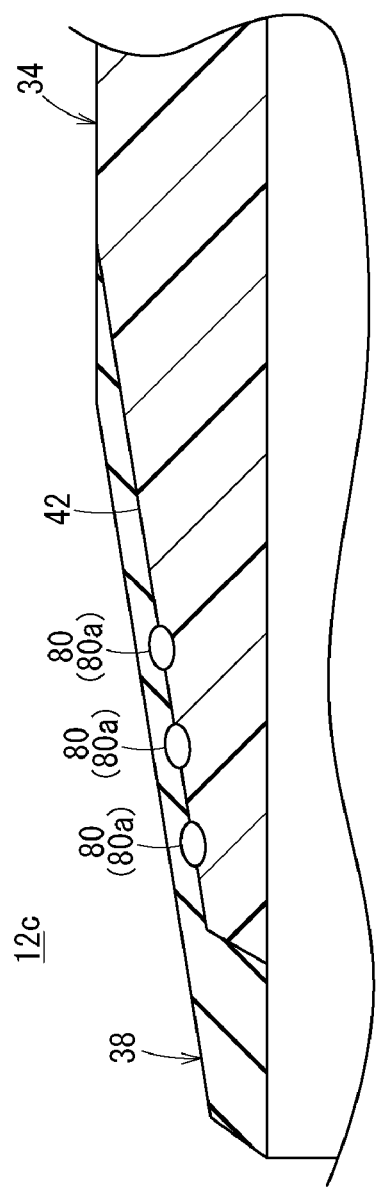
FIG. 13 is a cross-sectional view of a catheter having an echogenic portion.

In a catheter 12c illustrated in FIG. 13, the interface 42 between the catheter body 34 and the flexible portion 38 is provided with a region 80 having a different acoustic impedance from the catheter body 34 and the flexible portion 38. With this configuration, the above-described region 80 having the different acoustic impedance functions as an echogenic portion, and thus, it is possible to improve the visibility of the distal portion of the catheter 12 under ultrasound fluoroscopy. Hereinafter, the region 80 having the different acoustic impedances is referred to as an "echogenic portion 80a".

The echogenic portion 80a is provided on the proximal side of the portion of the flexible portion 38 present on the distal side of the most distal portion of the catheter body 34. With this configuration, it is possible to deter peeling at the interface 42 between the catheter body 34 and the flexible portion 38 when the catheter 12c is advanced with respect to the inner needle 16.

A shape of the echogenic portion 80a may have the same shape as the deformation suppressing member 54. The shape of the echogenic portion 80a may be granular. A material of the echogenic portion 80a may be the same as or different from that of the deformation suppressing member 54. The echogenic portion 80a is not necessarily rigid, and thus, may be air, gel, or the like.

When a granular body is used as the echogenic portion 80a, a glass bead is particularly preferable. When a test was performed by providing the glass bead as the echogenic portion 80a, favorable visibility was obtained with the glass bead having a diameter of 30 to 120 μm.

The first tube member 76, which is the material of the catheter body 34, or the second tube member 78, which is the material of the flexible portion 38, (or both) may be molded by extrusion molding while mixing the granular body that is to form the echogenic portion 80a therein.

Figure 14A:
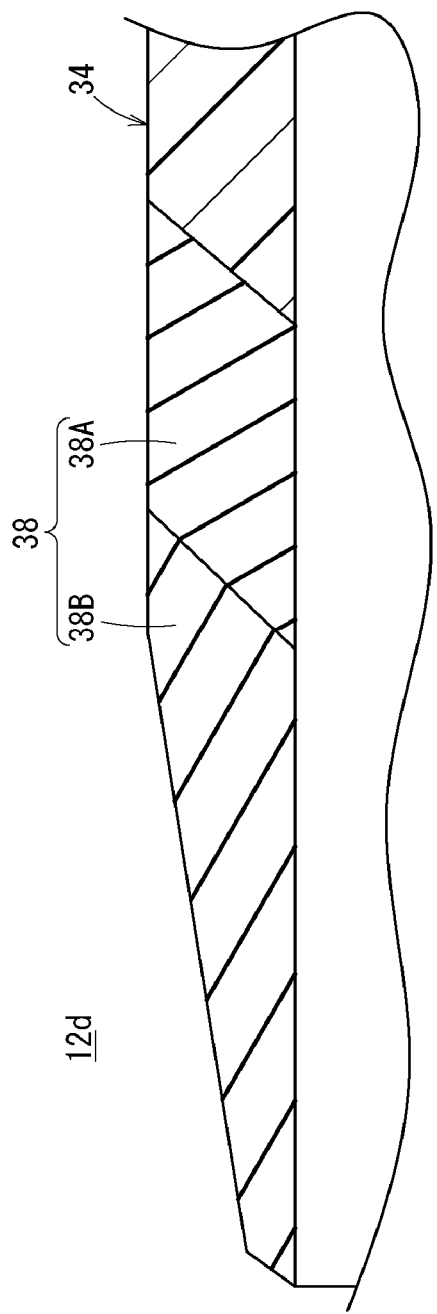
FIG. 14A is a cross-sectional view of a catheter provided with a flexible portion having a plurality of regions different in hardness.

In a catheter 12d illustrated in FIG. 14A, the flexible portion 38 has a first flexible portion 38A that is more flexible than the catheter body 34, and a second flexible portion 38B that is provided to be adjacent to the distal side of the first flexible portion 38A and is more flexible than the first flexible portion 38A. That is, an elastic modulus $k2a$ of the first flexible portion 38A, an elastic modulus $k2b$ of the second flexible portion 38B, and the elastic modulus $k1$ of the catheter body 34 have a relationship of $k1>k2a>k2b$.

With this configuration, the change in rigidity from the catheter body 34 to the flexible portion 38 can be made more gradual. Thus, it is possible to more favorably deter the distal end of the catheter 12d from being caught by the blood vessel back wall 50a at the time of inserting the catheter 12d into the blood vessel 50, and to deter the peeling of the interface 42 at the joint between the catheter body 34 and the flexible portion 38.

Figure 14B:
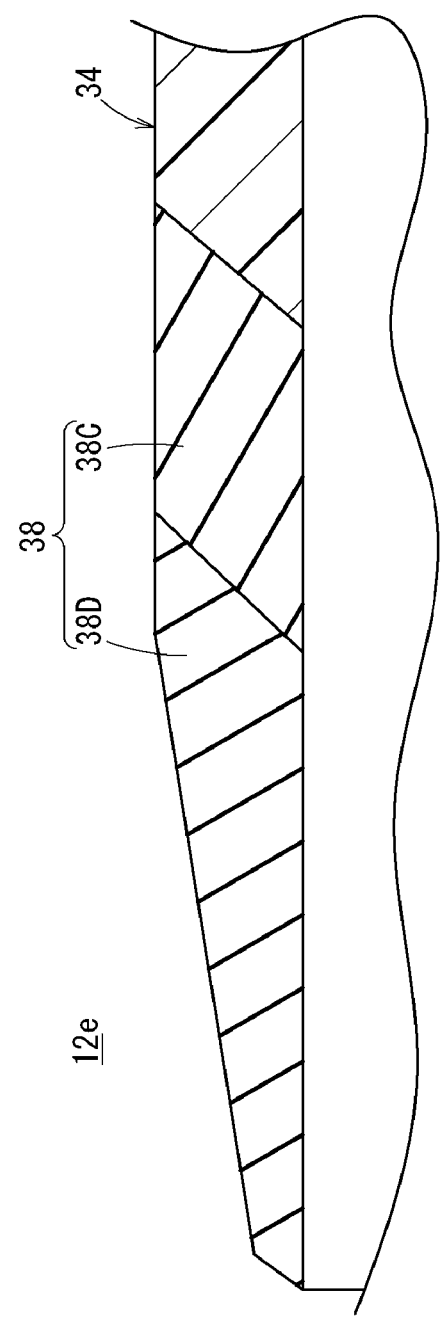
FIG. 14B is a cross-sectional view of a catheter provided with another flexible portion having a plurality of regions different in hardness.

In the catheter 12e illustrated in FIG. 14B, the flexible portion 38 has a first flexible portion 38C that is more flexible than the catheter body 34, and a second flexible portion 38D that is provided on the distal side of the first flexible portion 38C, includes a most distal portion of the catheter 12e, and is harder than the first flexible portion 38C. That is, an elastic modulus $k2c$ of the first flexible portion 38C, an elastic modulus $k2d$ of the second flexible portion 38D, and the elastic modulus $k1$ of the catheter body 34 have a relationship of $k1>k2d>k2c$. With this configuration, it is possible to suppress the crushing of the flexible portion 38 at the time of blood suction.

Figure 15:
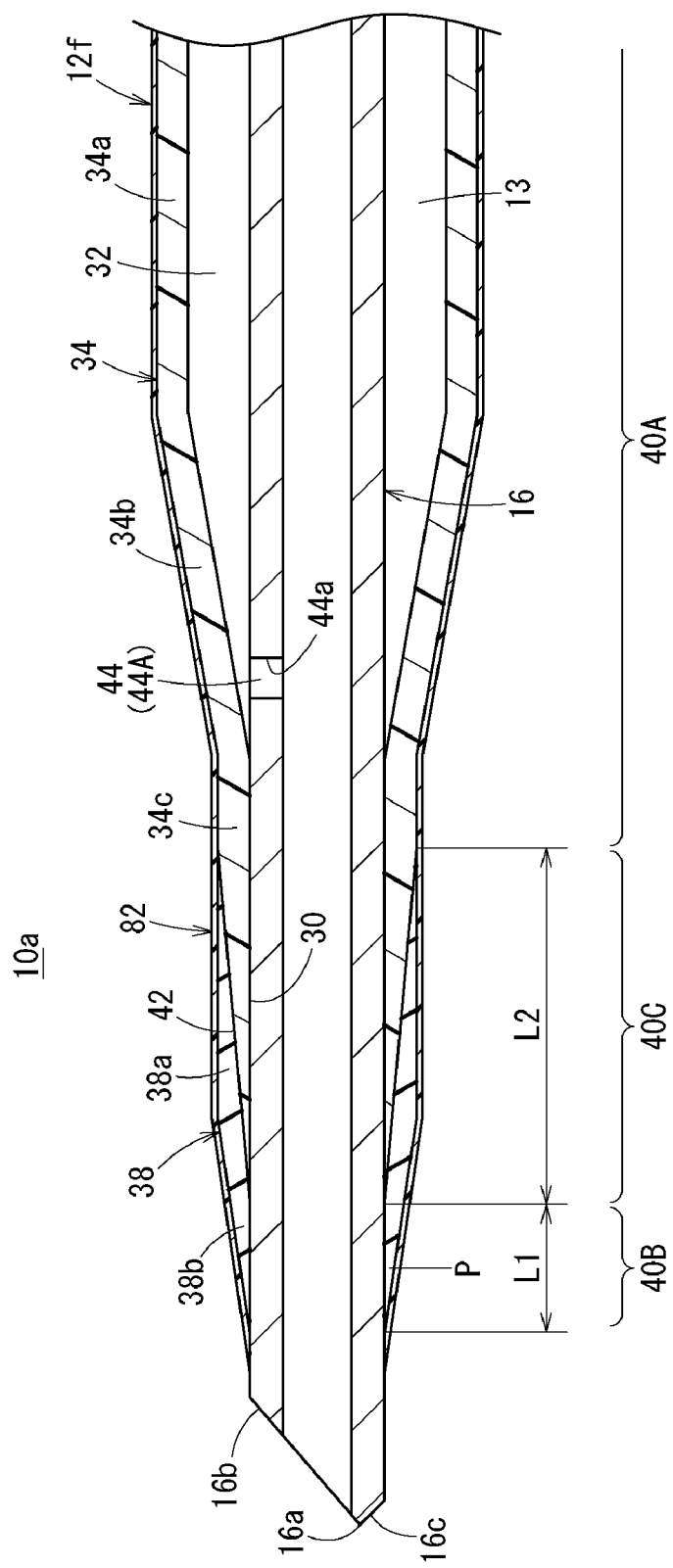
FIG. 15 is a cross-sectional view of a distal portion of a catheter assembly according to another embodiment of the present invention.

In a catheter 12f of a catheter assembly 10a illustrated in FIG. 15, a cover 82 is provided on an outer surface of the flexible portion 38 and an outer surface of the catheter body 34 such that a friction coefficient of an outer surface of the catheter 12f decreases. The cover 82 covers the whole outer surface of the catheter 12f. A friction coefficient T1 of the surface of the flexible portion 38, a friction coefficient T2 of the surface of the catheter body 34, and a friction coefficient T3 of the surface of the cover 82 have a relationship of T3<T2<T1. Examples of a material forming the cover 82 include silicone, methoxyethyl (meth) acrylate, and the like.

According to the catheter assembly 10a, the cover 82 is provided on the outer surface of the flexible portion 38, and the friction coefficient T3 of the surface of the cover 82 is smaller than the friction coefficient T1 of the surface of the flexible portion 38. Because the cover 82 having a small friction coefficient is provided on the outer surface of the flexible portion 38 in this manner, it is possible to suppress the curling of the soft flexible portion 38 at the time of puncturing the skin so that the cover 82 easily passes a skin puncture hole. In addition, at least a part of the flexible portion 38 is in close contact with the inner needle 16, and thus, the flexible portion 38 is less likely to be displaced from the inner needle 16 at the time of puncturing the skin and can be deterred from being curled.

According to the catheter assembly 10a, the cover 82 is provided on the outer surface of the flexible portion 38 and the outer surface of the catheter body 34, the friction coefficient T2 of the surface of the catheter body 34 is smaller than the friction coefficient T1 of the surface of the flexible portion 38, and the friction coefficient T3 of the surface of the cover 82 is smaller than the friction coefficient T2 of the surface of the catheter body 34. Thus, it is possible to suppress the curling of the soft flexible portion 38 at the time of puncturing the skin so that the cover 82 easily passes a skin puncture hole. In addition, because the friction coefficient T2 of the surface of the catheter body 34 is set to be small, it is possible to suppress an increase of a frictional force between the catheter 12f and the inner needle 16, and thus, an advancing operation is easily performed at the time of advancing the catheter 12f relative to the inner needle 16. Further, a difference between the friction coefficient T2 of the surface of the catheter body 34 and the friction coefficient T1 of the surface of the flexible portion 38 is not too large, and thus, the flexible portion 38 can be deterred from being curled inward at the time of advancing the catheter 12*f* relative to the inner needle 16.

Figure 16:
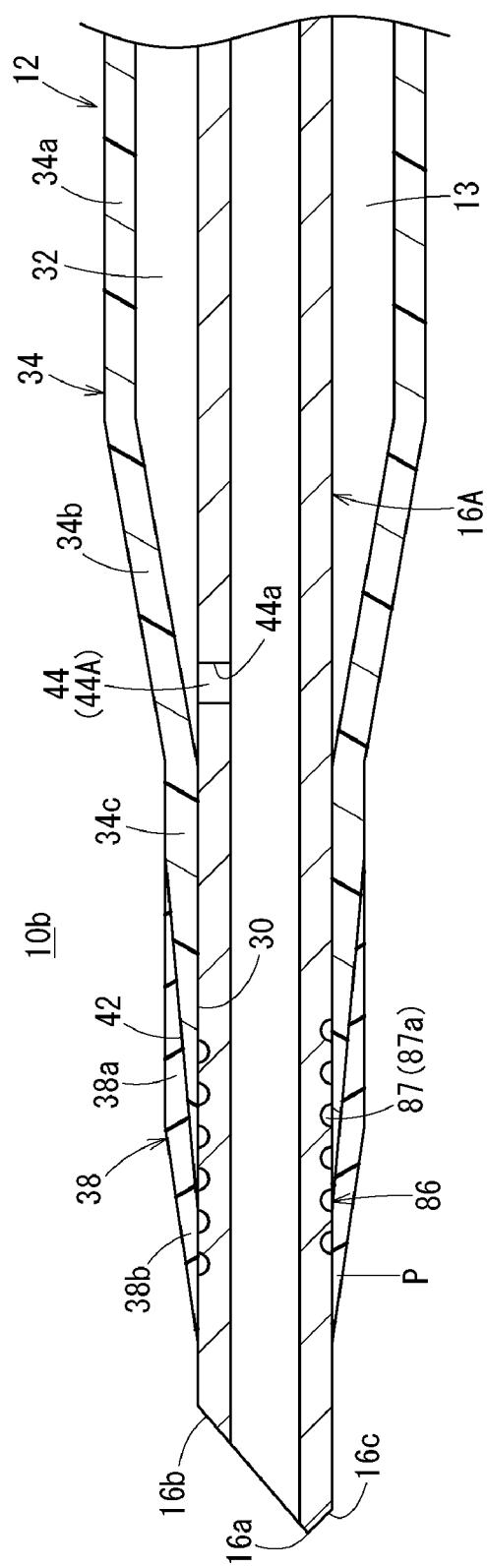
FIG. 16 is a cross-sectional view of a distal portion of a catheter assembly according to still another embodiment of the present invention.

In an inner needle 16A of a catheter assembly 10*b* illustrated in FIG. 16, a friction-increased shape portion 86 having at least one of a recess portion (groove) and a convex portion (protrusion) that increases a friction coefficient of an outer peripheral surface of the inner needle 16A is provided on the outer peripheral surface of the inner needle 16A. With this configuration, the friction coefficient of the outer peripheral surface of the inner needle 16A is increased, and thus, it is possible to deter the catheter 12 from being curled at the time of puncturing the skin with the catheter 12. The friction-increased shape portion 86 is provided at a position opposing an inner peripheral surface of the distal portion of the catheter 12.

In FIG. 16, the friction-increased shape portion 86 is a groove structure 87. More specifically, the groove structure 87 is a spiral groove 87*a*. Instead of the spiral groove 87*a*, a plurality of annular grooves may be provided at intervals in the axial direction.

When the friction-increased shape portion 86 is formed using the groove structure 87, the groove structure 87 is more preferably provided at a position overlapping the flexible portion 38 in the axial direction. When a human body is punctured with the catheter assembly 10*b* and the catheter 12 passes a skin puncture hole, a radial force from the outer surface of the catheter 12 to a central axis of the catheter 12 is applied so that the flexible portion 38 is deformed and the flexible portion 38 bites into the inside (recess portion) of the groove structure 87. Because a force, which causes the flexible portion 38 biting into the recess portion (the spiral groove 87*a* or the annular groove) of the groove structure 87 and holds the position of the flexible portion 38, overcomes a force generated as the flexible portion 38 is displaced from the inner needle 16A and deformed, it is possible to further deter the catheter 12 from being curled at the time of puncture.

The friction-increased shape portion 86 is not limited to the groove structure 87 but may be a protrusion structure. The protrusion structure may be a spiral protrusion, or may be a plurality of annular protrusions formed at intervals in the axial direction. The friction-increased shape portion 86 may be a roughened portion that has been subjected to processing to increase surface roughness. In this case, the roughened portion is a structure having a large number of fine recess shapes (grooves) and convex shapes (protrusions) that increase the friction coefficient of the outer peripheral surface of the inner needle 16A. When the roughened portion is provided, a position of the inner needle 16A can be confirmed by ultrasound irradiation at the time of puncturing the human body with the catheter assembly 10*b*.

The above-described groove structure 87 or protrusion structure may be configured to form a gap with respect to the inner peripheral surface of the catheter 12. As a result, ultrasound reflection of the ultrasound from an ultrasound imaging apparatus at a boundary of the gap is promoted, and a position of the groove structure 87 or the protrusion structure of the inner needle 16A can be recognized more favorably on a monitor of the ultrasound imaging apparatus.

The friction-increased shape portion 86 provided on the outer peripheral surface of the inner needle 16A is not necessarily provided at the position opposing the most distal portion of the flexible portion 38. As a result, the distal end of the flexible portion 38 is less likely to be curled at the time of puncture.

Figure 17:
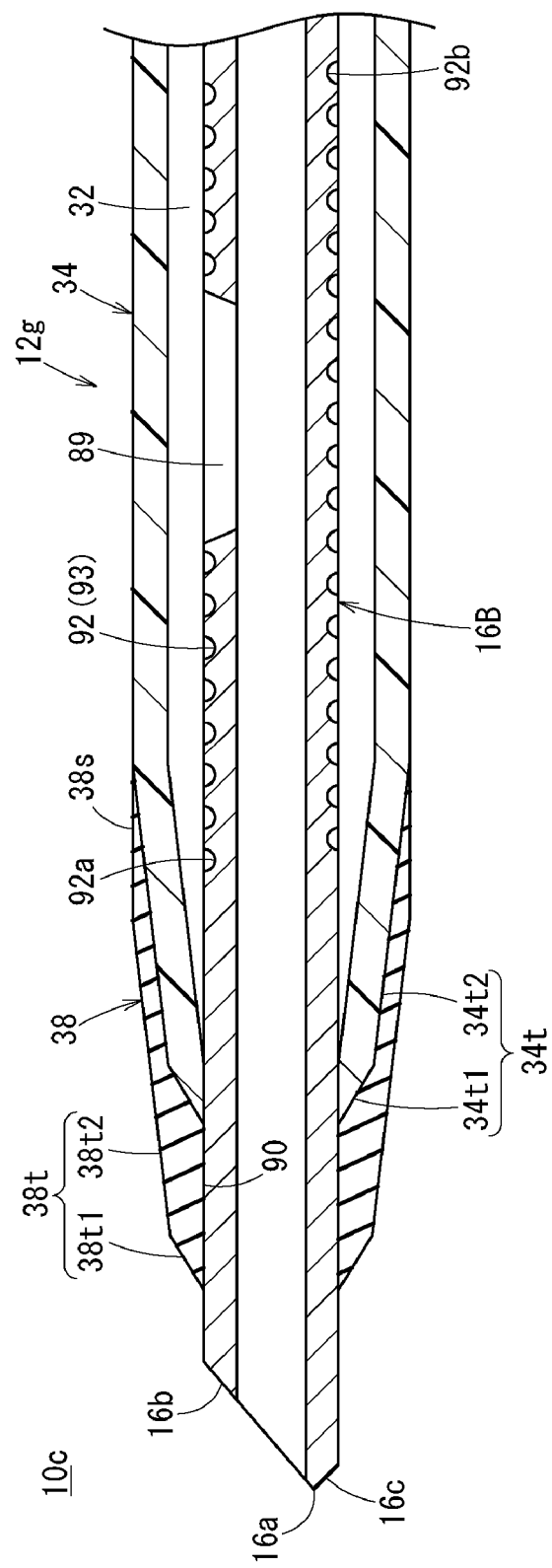
FIG. 17 is a cross-sectional view of a distal portion of a catheter assembly according to yet still another embodiment of the present invention.

A catheter 12*g* of a catheter assembly 10*c* illustrated in FIG. 17 has the catheter body 34 and the flexible portion 38 provided at the distal portion of the catheter body 34. The inner peripheral surface of the catheter body 34 and the inner peripheral surface of the flexible portion 38 are in close contact with an outer peripheral surface of an inner needle 16B over the whole circumference. A portion, which is in close contact with the outer peripheral surface of the inner needle 16B, at the distal portion of the catheter 12*g* constitutes a close contact portion 90.

The catheter body 34 has: a body tapered portion 34*t* that is inclined with respect to an axis of the catheter 12*g* such that an outer diameter decreases in the distal direction; and a flexible tapered portion 38*t* that is inclined with respect to the axis of the catheter 12*g* such that the outer diameter decreases in the distal direction.

The body tapered portion 34*t* is arranged on the radially inner side of the flexible tapered portion 38*t*. The body tapered portion 34*t* has a first body tapered portion 34*t*1 and a second body tapered portion 34*t*2 provided to be adjacent to the proximal side of the first body tapered portion 34*t*1. The flexible tapered portion 38*t* has a first flexible tapered portion 38*t*1 including a most distal portion of the catheter 12*g*, and a second flexible tapered portion 38*t*2 provided to be adjacent to the proximal side of the first flexible tapered portion 38*t*1.

The first body tapered portion 34*t*1 has an inclination angle at an outer peripheral surface with respect to the axis of the catheter 12*g* larger than that of the second body tapered portion 34*t*2. According to this configuration, the inclination angle of the first body tapered portion 34*t*1 is relatively large, and thus, it is possible to support the flexible portion 38 from the inner side at the time of blood suction and to suppress a collapse of the flexible portion 38. Because the inclination angle of the second body tapered portion 34*t*2 is relatively small, the gradual transition from a physical property of the flexible portion 38 to a physical property of the catheter body 34 becomes possible, and a kink of the catheter 12*g* can be suppressed.

The first flexible tapered portion 38*t*1 has an inclination angle at an outer peripheral surface with respect to the axis of the catheter 12*g* larger than that of the second flexible tapered portion 38*t*2. According to this configuration, the first flexible tapered portion 38*t*1 is relatively thick, and thus, it is possible to suppress the curling of the distal end of the catheter 12*g* at the time of puncture. The second flexible tapered portion 38*t*2 has the relatively small inclination angle, and thus, the penetration resistance can be reduced.

The inclination angle of the first body tapered portion 34*t*1 is slightly smaller than the inclination angle of the first flexible tapered portion 38*t*1. The first body tapered portion 34*t*1 is arranged on the radially inner side of the second flexible tapered portion 38*t*2. A most proximal portion of the second flexible tapered portion 38*t*2 is positioned on the proximal side of a most proximal portion of the first body tapered portion 34*t*1. The flexible portion 38 has a straight portion 38*s*, which is parallel to the axis of the catheter 12*g*, on the proximal side of the second flexible tapered portion 38*t*2.

The flow path 32 for flashback confirmation is formed between the catheter 12*g* and the inner needle 16B. The inner needle 16B is provided with a side hole 89 that communicates with the flow path 32 to introduce blood into the flow path 32. The side hole 89 (specifically, a most distal portion of the side hole 89) is provided on the proximal side of a most distal portion of the body tapered portion 34*t* (the most distal portion of the catheter body 34). With this configuration, the side hole 89 is provided at a position opposing the relatively hard catheter body 34. Therefore, it is possible to deter the catheter 12g from blocking the side hole 89 at the time of puncture, and thus, it is possible to easily confirm the flashback of blood. The side hole 89 is provided on the proximal side of the second body tapered portion 34t2.

An inner peripheral surface of the flexible tapered portion 38t and an inner peripheral surface of the first body tapered portion 34t1 are in close contact with the outer peripheral surface of the inner needle 16B. That is, the close contact portion 90 is constituted by the inner peripheral surface of the flexible tapered portion 38t and the inner peripheral surface of the first body tapered portion 34t1.

An ultrasound reflection promoting portion 92 having an uneven shape (step shape) is provided on the outer peripheral surface of the inner needle 16B. In FIG. 17, the ultrasound reflection promoting portion 92 is a spiral groove 93 that is recessed with respect to the outer peripheral surface of the inner needle 16B. The ultrasound reflection promoting portion 92 may be a spiral protrusion protruding to the radially outer side from the outer peripheral surface of the inner needle 16B. The ultrasound reflection promoting portion 92 may be configured using a plurality of ring-shaped grooves or a plurality of ring-shaped protrusions arranged at intervals in the axial direction.

A most distal portion 92a of the ultrasound reflection promoting portion 92 is positioned on the distal side of the side hole 89. The most distal portion 92a of the ultrasound reflection promoting portion 92 is positioned on the distal side of the most proximal portion of the second flexible tapered portion 38t2. The most distal portion 92a of the ultrasound reflection promoting portion 92 is positioned on the distal side of a most proximal portion of the second body tapered portion 34t2.

The most distal portion 92a of the ultrasound reflection promoting portion 92 is provided on the proximal side of a proximal portion of the close contact portion 90. According to this configuration, the close contact portion 90 and the ultrasound reflection promoting portion 92 do not overlap each other so that the uneven shape of the ultrasound reflection promoting portion 92 does not contribute to a resistance at the time of removing the inner needle 16B, and the removal operation is stabilized.

A most proximal portion 92b of the ultrasound reflection promoting portion 92 is positioned on the proximal side of the side hole 89. The most proximal portion 92b of the ultrasound reflection promoting portion 92 is positioned on the proximal side of the most proximal portion of the second flexible tapered portion 38t2. The most proximal portion 92b of the ultrasound reflection promoting portion 92 is positioned on the distal side of the most proximal portion of the second body tapered portion 34t2.

In the catheter 12g, the catheter body 34 has transparency that allows the inside of the catheter body 34 to be visible. The flexible portion 38 may have a color that is more easily visible than the catheter body 34. When configured in this manner, the flexible portion 38 is colored to be easily noticeable while securing the flashback visibility by giving the transparency to the catheter body 34, it is easy to perform puncture with respect to a target blood vessel. In addition, it is easy to understand that the flexible portion 38 is provided at the distal portion of the catheter 12g, and thus, it is possible to appeal to the user that a function of deterring a blood vessel injury is high.

It is preferable that at least the flexible portion 38 between the catheter body 34 and the flexible portion 38 have an X-ray contrast property. If both the catheter body 34 and the flexible portion 38 have X-ray contrast properties, the flexible portion 38 preferably has a higher X-ray contrast property than the catheter body 34. A contrast layer in the case where the flexible portion 38 has the contrast property may be provided, for example, in any form of a stripe shape, an intermediate layer in the radial direction, or the whole layer. When the stripe-shaped contrast layer is provided in the flexible portion 38, the flexible portion 38 can have the higher X-ray contrast property than the catheter body 34 by making the number of stripes thereof larger than that in a stripe-shaped contrast layer provided in the catheter body 34.

A double needle (Sample 1 to 10) consisting of a catheter (1.01 to 1.12 mm) and an inner needle (22G) respectively obtained by applying the configurations of the catheter 12g and the inner needle 16B in the above-described catheter assembly 10 was prepared, and a curling test, a suction test, a penetration resistance test, and a stuck test to be described below were performed. Test results are shown in FIG. 18.

Samples 1 to 9 had flexible portions (soft tips) at distal portions, respectively, and Sample 10 had no flexible portion at its tip. In Samples 1 to 9, a catheter body was made of relatively hard urethane, and the flexible portion was made of relatively soft urethane. In Sample 10, the catheter was made of only the same hard urethane as the catheter body.

In Samples 1 to 9, a "first taper angle" is an inclination angle of a first flexible tapered portion of the flexible portion, and a "second taper angle" is an angle of a second flexible tapered portion of the flexible portion. Sample 10 has no flexible portion, but has a first tapered portion corresponding to the first flexible tapered portion, and a "first taper angle" in a table is an inclination angle of the first tapered portion. Similarly, a "second taper angle" in Sample 10 in the table is an angle of the second tapered portion corresponding to the second flexible tapered portion. Samples 1 to 10 have different second taper angles. Samples 1 to 9 have different distal end tip lengths (distances from most distal portions of the catheter bodies to most distal portions of the flexible portions).

1. Curling Test

In the curling test, a pig skin and cowhide were used as objects to be punctured, and the object to be punctured was punctured with a sample. The pig skin was used assuming a human skin with standard hardness. The pig skin was punctured at a puncture angle of 20°, and then, its appearance was visually observed. The cowhide was used assuming a stiff human skin. The cowhide was punctured at a puncture angle of 90°, and then, its appearance was visually observed. It was determined as "OK" when the catheter was insertable into the object to be punctured, and it was determined as "NG" when the distal end of the catheter was curled on a surface of the object to be punctured and was not insertable. In the curling test, it is considered that it is disadvantageous if the distal end tip length is long, but the curling does not depend on the second taper angle.

2. Suction Test

In the suction test, a 5 mL syringe was connected to a catheter hub via an extension tube, and viscosity-adjusted simulated blood at 37° C. was suctioned at a rate of 1 mL/sec to confirm presence or absence of crushing of a catheter. It was determined as "OK" when the crushing did not occur, and it was determined as "NG" when the crushing occurred. In the suction test, it is considered that it is disadvantageous if the distal end tip length is long, and it is disadvantageous if the second taper angle is small.

3. Penetration Resistance Test

A polyethylene sheet having a thickness of 50 μm was punctured with each sample at 10 mm/min, and a resistance value (N) applied to each sample was measured by an indentation load tester (Autograph AG-1 kNX manufactured by Shimadzu Corporation). It is considered that the penetration resistance depends on an appearance shape (because the resistance is maximized at a most distal end). In addition, it is considered that the penetration resistance also depends on the first taper angle.

4. Stuck Test

In the stuck test, the following Tests (1) and (2) were performed.

Test (1)

From a state where a distal end of a double needle was brought close to a silicone sheet having a thickness of 1 mm (obtained assuming a blood vessel back wall) (a distance from a sheet to a needle tip of an inner needle was 2 mm), and only the catheter was advanced to abut on the sheet to confirm whether a distal portion of the catheter could push the catheter forward by changing its direction on a surface of the sheet. It was recognized as a non-insertable state when the catheter abutted on the sheet so that it was not allowed to push the catheter further forward. A puncture angle was increased at 5-degree intervals, and the maximum angle at which the insertion was possible was recorded.

Test (2)

The puncture angle was fixed at 45°, which is a clinically approximating condition (to actual puncture), a canine blood vessel (inferior vena cava) was punctured with a sample (only Sample 1 and 10) in the same manner as in Test (1) to confirm whether a catheter could be pushed forward to be inserted into the blood vessel. Because one that was insertable in Test (2) (Sample 3) was inserted up to 60° in Test (1), those having the penetration angles of 60° or larger in Test (1) were determined as "OK". Because one that was non-insertable in Test (2) (Sample 10) was inserted up to 50° in Test (1), those having the penetration angles of 50° or smaller in Test (1) were determined as "NG".

In the stuck test, it is considered that it is advantageous if the distal end tip length is long, and it is advantageous if the second taper angle is small.

Based on the test results shown in FIG. 18, only Sample 3 showed favorable results in all the tests. A desired range of the distal end tip length is longer than 0.6 mm and shorter than 1.1 mm. In terms of an outer diameter (1.01 to 1.12 mm) of the catheter used for the test, a distal end tip length/catheter outer diameter of the present embodiment is desirably longer than 0.54 and shorter than 1.08.

Figure 19:
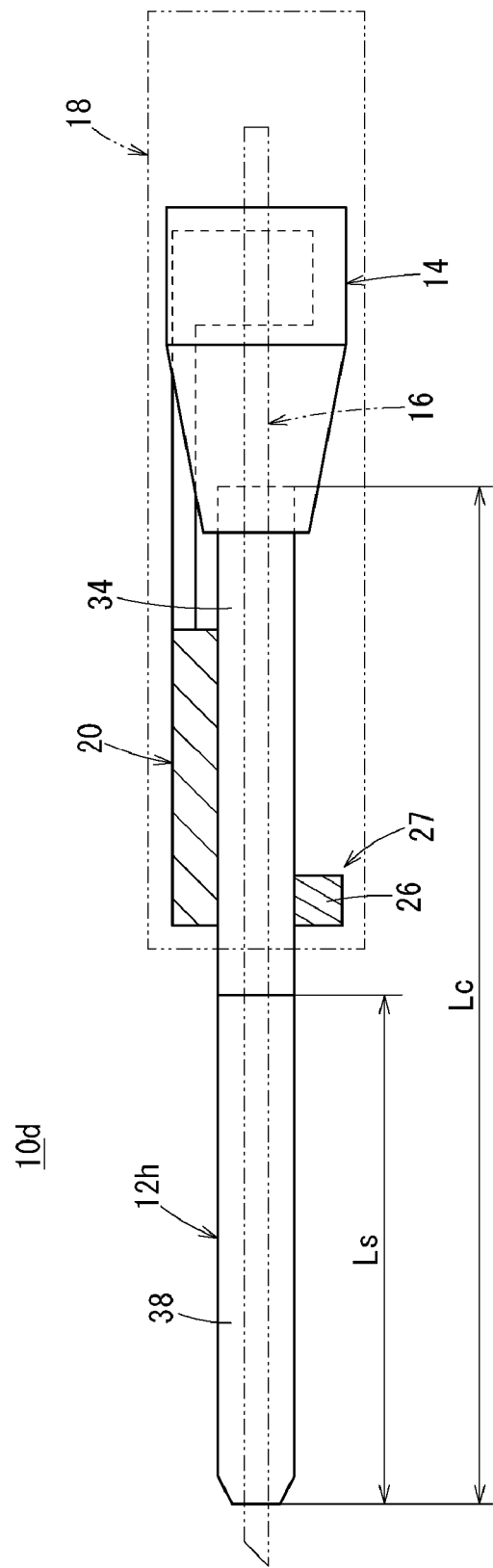
FIG. 19 is an overall schematic view of a catheter assembly according to even yet still another embodiment of the present invention.

In a catheter assembly 10$d$ illustrated in FIG. 19, a catheter 12$h$ has the catheter body 34 and the flexible portion 38 provided at a distal portion of the catheter body 34. A ratio of a total length Lc of the catheter body 34 to a length Ls of the flexible portion 38 is 2 to 1. Therefore, when the total length Lc of the catheter body 34 is, for example, 50 mm, the length Ls of the flexible portion 38 is 25 mm.

As illustrated in FIG. 19, the catheter assembly 10$d$ includes the deflection suppressing mechanism 27 that is capable of supporting the catheter 12$h$ at the time of puncture and suppressing deflections of the inner needle 16 and the catheter 12$h$. This deflection suppressing mechanism 27 has the same configuration as the deflection suppressing mechanism 27 in the above-described catheter assembly 10 (see FIG. 1), and is constituted by the support member 26 provided at the distal portion of the housing 24 and the catheter operation member 20 mounted on the catheter hub 14.

The deflection suppressing mechanism 27 is arranged on the proximal side of the flexible portion 38 (the most proximal portion of the flexible portion 38) in an initial state (a state before the catheter 12$h$ is advanced with respect to the inner needle 16) of the catheter assembly 10$d$ illustrated in FIG. 19. With this configuration, it is possible to deter the deflection suppressing mechanism 27 from damaging the flexible portion 38 at the time of advancing the catheter 12$h$ with respect to the inner needle 16.

The deflection suppressing mechanism 27 is preferably arranged on the proximal side of the flexible portion 38 in the vicinity of the flexible portion 38 in the initial state of the catheter assembly 10$d$. As a result, the deflection suppressing mechanism 27 can support the catheter 12$h$ at a position on the distal side as much as possible within a range not touching the flexible portion 38, and thus, can appropriately exhibit the function of suppressing the deflections of the inner needle 16 and the catheter 12$h$ while deterring the flexible portion 38 from being damaged.

The deflection suppressing mechanism 27 may be configured by only any one of the support member 26 and the catheter operation member 20. The deflection suppressing mechanism 27 may be configured so as to surround the whole circumference of the catheter 12$h$.

The present invention is not limited to the above-described embodiments, and various modifications can be made within a scope not departing from a gist of the present invention.

What is claimed is:

1. A catheter assembly comprising:
   a catheter; and
   a rigid inner needle inserted through the catheter;
   wherein the catheter comprises:
      a catheter body; and
      a flexible portion that is located at a distal portion of the catheter body and forms a most distal portion of the catheter, wherein the flexible portion comprises:
         a straight portion that has an outer diameter that is constant along an axial direction of the catheter, and
         a tapered portion that extends from the straight portion in a distal direction, and that has an outer diameter that decreases in the distal direction;
   wherein an elastic modulus of the catheter body is greater than an elastic modulus of the flexible portion;
   wherein the catheter has a mixed region in which the catheter body and the flexible portion overlap each other in a radial direction;
   wherein the flexible portion is formed of a material chosen from a group consisting of natural rubber, butyl rubber, isoprene rubber, butadiene rubber, styrene-butadiene rubber, silicone rubber, polyurethane, polyester, polyamide, olefin, or styrene; and
   wherein in a region distal of the catheter body, an inner peripheral surface of the flexible portion and the mixed region is in direct contact with an outer peripheral surface of the inner needle in a liquid-tight manner over an entire periphery of the inner needle.

2. The catheter assembly of claim 1, wherein:
   an interface between the catheter body and the flexible portion in the mixed region is formed in a tapered shape that is inclined at a constant angle with respect to an axis of the catheter.

3. The catheter assembly of claim 1, further comprising:
   a cover provided on an outer surface of the flexible portion; and wherein a friction coefficient of a surface of the cover is smaller than a friction coefficient of a surface of the flexible portion.

4. The catheter assembly of claim 3, wherein:
a material of the cover comprises at least one of silicone, methoxyethyl, or acrylate.

5. The catheter assembly of claim 1, wherein:
a flow path for flashback confirmation is formed between the catheter and the inner needle; and
the flow path extends to a proximal opening of the catheter.

6. The catheter assembly of claim 1, wherein:
the flexible portion comprises a deformation suppressing member that suppresses radial deformation.

7. The catheter assembly of claim 6, wherein:
the deformation suppressing member is located on the inner peripheral surface or an outer peripheral surface of the flexible portion.

8. The catheter assembly of claim 6, wherein:
the deformation suppressing member is located on the inner peripheral surface or an outer peripheral surface of the catheter body in the mixed region.

9. The catheter assembly of claim 6, wherein:
the deformation suppressing member comprises at least one of a ring or coil that at least partially surrounds a portion of the catheter.

10. The catheter assembly of claim 1, wherein:
the catheter body is transparent such that an inside of the catheter body is visible through the catheter body; and
the flexible portion is colored such that the flexible portion is more easily visible than the catheter body.

11. The catheter assembly of claim 1, wherein:
the flexible portion has an X-ray contrast property that is higher than that of the catheter body.

12. The catheter assembly of claim 1, wherein:
a flow path for flashback confirmation is formed between the catheter and the inner needle;
the inner needle comprises an introduction path that communicates with the flow path to introduce blood into the flow path; and
the introduction path is located proximal of the mixed region.

13. The catheter assembly of claim 1, wherein:
an entirety of the catheter is coated seamlessly with a single coating material.

14. The catheter assembly of claim 1, wherein:
a creep strain of the catheter body is greater than a creep strain of the flexible portion.

15. The catheter assembly of claim 1, wherein:
an axial length of the mixed region is in a range of 1.0 to 5.0 mm.

16. The catheter assembly of claim 1, wherein:
an axial length of the flexible portion is in a range of 0.3 to 5.0 mm.

* * * * *